United States Patent
Fenyvesi et al.

(10) Patent No.: US 8,309,116 B2
(45) Date of Patent: Nov. 13, 2012

(54) PERSONAL CARE AND COSMETICS COMPOSITIONS COMPRISING BIOLOGICALLY-BASED MONO AND DI ESTERS

(75) Inventors: Gyorgyi Fenyvesi, Wilmington, DE (US); Ann Wehner, Hockessin, DE (US); Melissa Joerger, Newark, DE (US); Raja Hari Prasad R. Poladi, Bear, DE (US)

(73) Assignee: DuPont Tate & Lyle Bio Products Company, LLC, Wilmington, DE (US)

( * ) Notice: Subject to any disclaimer, the term of this patent is extended or adjusted under 35 U.S.C. 154(b) by 653 days.

(21) Appl. No.: 12/579,538

(22) Filed: Oct. 15, 2009

(65) Prior Publication Data

US 2010/0034761 A1  Feb. 11, 2010

Related U.S. Application Data

(63) Continuation of application No. 11/705,227, filed on Feb. 12, 2007, now abandoned.

(60) Provisional application No. 60/772,471, filed on Feb. 10, 2006, provisional application No. 60/772,194, filed on Feb. 10, 2006, provisional application No. 60/772,193, filed on Feb. 10, 2006, provisional application No. 60/772,111, filed on Feb. 10, 2006, provisional application No. 60/772,120, filed on Feb. 10, 2006, provisional application No. 60/772,110, filed on Feb. 10, 2006, provisional application No. 60/772,112, filed on Feb. 10, 2006, provisional application No. 60/846,948, filed on Sep. 25, 2006, provisional application No. 60/853,920, filed on Oct. 24, 2006, provisional application No. 60/859,264, filed on Nov. 15, 2006, provisional application No. 60/872,705, filed on Dec. 4, 2006, provisional application No. 60/880,824, filed on Jan. 17, 2007.

(51) Int. Cl.
  *A61F 2/00* (2006.01)
  *A01N 37/00* (2006.01)

(52) U.S. Cl. .................................. 424/428; 514/506

(58) Field of Classification Search .................. None
  See application file for complete search history.

(56) References Cited

U.S. PATENT DOCUMENTS

| | | | | |
|---|---|---|---|---|
| 6,555,700 B1 * | 4/2003 | Horrobin et al. | ............... | 554/227 |
| 6,726,887 B1 * | 4/2004 | Sugarman | ....................... | 423/24 |
| 2004/0105899 A1 * | 6/2004 | Dowdle et al. | ................ | 424/725 |
| 2005/0154114 A1 * | 7/2005 | Hale | ............. | 524/436 |
| 2006/0035808 A1 * | 2/2006 | Ahmed et al. | ................ | 510/499 |
| 2006/0110610 A1 * | 5/2006 | Matsutani et al. | ............. | 428/447 |
| 2006/0110810 A1 * | 5/2006 | Rajgarhia et al. | ............. | 435/139 |

FOREIGN PATENT DOCUMENTS

| | | | |
|---|---|---|---|
| EP | 1604647 A1 | * | 12/2005 |
| JP | 200515401 | * | 1/2005 |

OTHER PUBLICATIONS

Chen et al. "Cyclization During Polyesterifications: Isolation of an 18-member Ring Compund from Reaction of Phthalic Anhydride with 2,2-dimethyl-1,3-propandiol", Journal of Applied Polymer Science, 1990, vol. 41, Issue 9-10, pp. 2517-2520.*
Fung et al. "Evolution of Carbon Sinks in a Changing Climate", PNAS, Aug. 9, 2005, vol. 12, No. 32, pp. 11201-11206.*
Jabrane et al. "Study of the Thermal Behaviour of 1,3-propandiol and its Aqueous Solution", Themochimica Acta 311, 1998, pp. 121-127.*
Paster et al. "Industrial Bioproducts: Today and Tomorrow", Prepared by Energetic, Inc. For the US Department of Energy, Jul. 2003, pp. 1-93.*
Huang et al. "Production of 1,3-propanediol by Diebsiella Pneumoniae", Applied Biochemistry and Biotechnology, vol. 96-100, 2002, pp. 687-698.*

* cited by examiner

*Primary Examiner* — Lezah Roberts
*Assistant Examiner* — Nannette Holloman
(74) *Attorney, Agent, or Firm* — McCarter & English

(57) ABSTRACT

Personal care compositions comprising esters of 1,3-propanediol and acceptable carriers are provided. The esters can have at least 3% biobased carbon, and the compositions can further comprise 1,3-propanediol that is biologically-derived. Also provided are processes for producing personal care compositions comprising esters of 1,3-propanediol and acceptable carriers. The processes comprise providing biologically produced 1,3-propanediol, contacting the 1,3-propanediol with organic acids, which produces the esters, recovering the esters, and incorporating the esters into personal care formulations. Also provided are processes of making a personal care composition comprising providing an ester of 1,3 propanediol and mixing the ester with an acceptable carrier to form a personal care composition.

14 Claims, 7 Drawing Sheets

PERSONAL CARE AND COSMETICS COMPOSITIONS COMPRISING BIOLOGICALLY-BASED MONO AND DI ESTERS

CROSS REFERENCE TO RELATED APPLICATIONS

This application is a continuation of U.S. patent application Ser. No. 11/705,227, filed Feb. 12, 2007, now abandoned. This application also claims the benefit of U.S. Provisional Application Ser. No. 60/772,471, filed Feb. 10, 2006; U.S. Provisional Application No. 60/772,194, filed Feb. 10, 2006, U.S. Provisional Application No. 60/772,193, filed Feb. 10, 2006, U.S. Provisional Application No. 60/772,111, filed Feb. 10, 2006, U.S. Provisional Application No. 60/772,120, filed Feb. 10; 2006, U.S. Provisional Application No. 60/772,110 filed Feb. 10, 2006, U.S. Provisional Application No. 60/772,112, filed Feb. 10, 2006, U.S. Provisional Application No. 60/846,948, filed Sep. 25, 2006, U.S. Provisional Application No. 60/853,920, filed Oct. 24, 2006, U.S. Provisional Application No. 60/859,264, filed Nov. 15, 2006, U.S. Provisional Application No. 60/872,705, filed Dec. 4, 2006, U.S. Provisional Application No. 60/880,824, filed Jan. 17, 2007, the disclosures of which are all expressly incorporated herein by reference in their entireties.

FIELD OF THE INVENTION

The invention relates to the field of personal care products, which includes cosmetics, crèmes, shampoos, body wash, liquid soap, moisturizers, deodorants, toiletries, and skin care products. More specifically, the invention relates to personal care compositions comprising biologically-derived 1,3-propanediol esters.

BACKGROUND OF THE INVENTION

For many solutions, crèmes and soft solids the active ingredient is only a small portion of the product. Much of these products are composed of other ingredients, adjuvants, which provide benefit to the product. These adjuvants convey benefit to the product in a variety of ways. Some adjuvants allow the active ingredient to be applied in a particular manner, by changing or assisting to change the concentration, feel or viscosity of the solution. Such classes of this type of adjuvants are emulsifiers, conditioners, surfactants, structurants, and thickeners. Other adjuvants protect the active ingredient or the product as whole from disintegrating from its desired form. Humectants, temperature stabilizers and chemical stabilizers are classes of this type of adjuvant. Still other adjuvants provide an aesthetic appeal to the appearance of product. Adjuvants of this type can be further classified as opacificers, colorants or pearlizing agents.

Many different substances have been experimented with for their ability to act as an adjuvant of one type or another, even to fulfill multiple roles. Both naturally occurring substances and chemically synthesized substances have been experimented with. For instance, waxes, oils, alcohols, fatty acids, petroleum products, esters, salts and polymers have all been used in the past. However, to this date there is a desire for an adjuvant that can be used in various roles and is created in a manner that is pleasing to the consumer.

Consumers and manufacturers are increasingly concerned with the environmental impact of all products. The effort towards environmental impact awareness is a universal concern, recognized by government agencies. The Kyoto Protocol amendment to the United Nations Framework Convention on Climate Change (UNFCCC) currently signed by 156 nations is one example of a global effort to favor safer environmental manufacturing over cost and efficiency. Consumers are increasingly selective about the origins of the products they purchase. The 2004 Co-operative Bank's annual Ethical Consumerism Report (www.co-operativebank.co.uk) disclosed a 30.3% increase in consumer spending on ethical retail products (a general classification for environmental safe, organic and fair trade goods) between 2003 and 2004 while total consumer spending during the same period rose only 3.7%.

One of the single greatest environmental concerns to consumers is the global warming effect and greenhouse gases that contribute to the effect. Greenhouse gases are gases that allow sunlight to enter the atmosphere freely. When sunlight strikes the Earth's surface, some of it is reflected back towards space as infrared radiation. Greenhouse gases absorb this infrared radiation and trap the heat in the atmosphere. Over time, the amount of energy sent from the sun to the Earth's surface should be about the same as the amount of energy radiated back into space, leaving the temperature of the Earth's surface roughly constant. However, increasing the quantity of greenhouse gases above the quantity that existed before the rise of human industrialization is thought to increase the retained heat on the Earth's surface and produce the global warming observed in the last two centuries.

Carbon dioxide is singled out as the largest component of the collection of greenhouse gases in the atmosphere. The level of atmospheric carbon dioxide has increased 50% in the last two hundred years. Any further addition of carbon dioxide to the atmosphere is thought to further shift the effect of greenhouse gases from stabilization of global temperatures to that of heating. Consumers and environmental protection groups alike have identified industrial release of carbon into the atmosphere as the source of carbon causing the greenhouse effect. Only organic products composed of carbon molecules from renewably based sources such as plant sugars and starches and ultimately atmospheric carbon are considered to not further contribute to the greenhouse effect, when compared to the same organic molecules that are petroleum or fossil fuel based.

In addition to adding carbon dioxide to the atmosphere, current methods of industrial production of propanediols produce contaminants and waste products that include among them sulfuric acid, hydrochloric acid, hydrofluoric acid, phosphoric acid, tartaric acid, acetic acids, alkali metals, alkaline earth metals, transitional metals and heavy metals, including Iron, cobalt, nickel, copper, silver, molybdenum, tungsten, vanadium, chromium, rhodium, palladium, osmium, iridium, rubidium, and platinum (U.S. Pat. Nos. 2,434,110, 5,034,134, 5,334,778, and 5,10,036).

There is a need for all manufacturers to provide products with reduced environmental impacts, and to especially consider the carbon load on the atmosphere. There is also an environmental advantage for manufacturers to provide products of renewably based sources. Further, there is a need for a proven personal care adjuvant, which is produced with no or little increase to the present carbon-dioxide level in the environment.

Published U.S. Patent Application No. 2005/0069997 discloses a process for purifying 1,3-propanediol from the fermentation broth of a cultured *E. coli* that has been bioengineered to synthesize 1,3-propanediol from sugar. The basic process entails filtration, ion exchange and distillation of the fermentation broth product stream, preferably including chemical reduction of the product during the distillation procedure. Also provided are highly purified compositions of 1,3-propanediol.

SUMMARY OF THE INVENTION

Personal care compositions comprising esters of 1,3-propanediol and acceptable carriers are provided. The esters can have at least 3% biobased carbon, and the compositions can further comprise 1,3-propanediol that is biologically-derived. Also provided are processes for producing personal care compositions comprising esters of 1,3-propanediol and acceptable carriers. The processes comprise providing biologically produced 1,3-propanediol, contacting the 1,3-propanediol with organic acids, which produces the esters, recovering the esters, and incorporating the esters into personal care formulations. Also provided are processes of making a personal care composition comprising providing an ester of 1,3 propanediol and mixing the ester with an acceptable carrier to form a personal care composition.

BIOLOGICAL DEPOSITS

Figure 1:
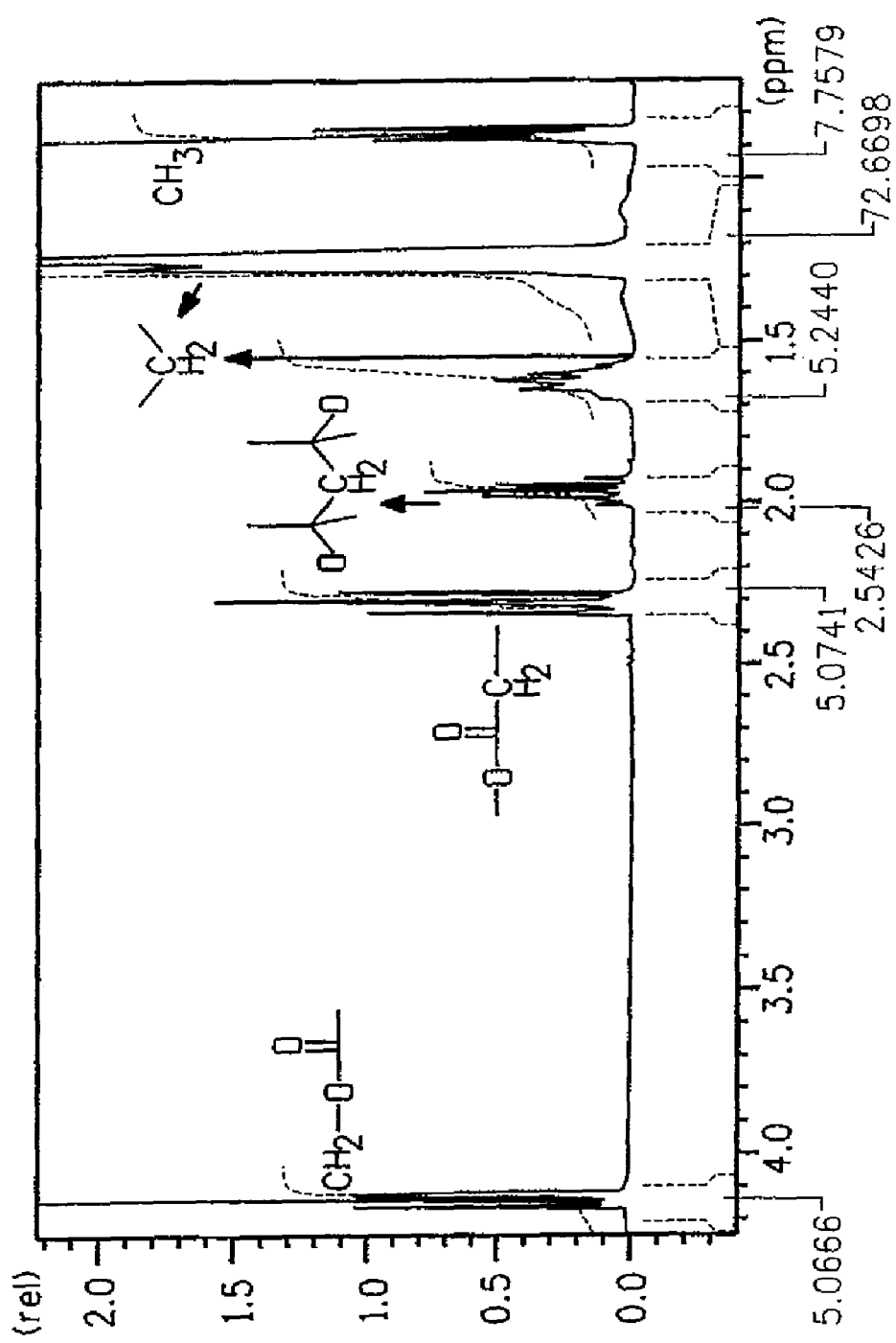
FIG. 1 is diagram of nuclear magnetic resonance spectra of the products obtained in Example 3. The figure plots the following values: ($CDCl_3$): $\delta$=0.88 (t, $CH_3$—$CH_2$, 6H), 1.26 (t, $CH_2$—$CH_2$—$CH_2$, 28H), 1.61 (t, $\underline{C}H_2$—$CH_2$—C=O, 4H), 1.97 (t, —O—$CH_2$—$CH_2$—$\underline{CH_2}$—O, 2H), 2.28 (t, C$\underline{H_2}$—C=O, 4H), 4.15 (t, C(=O)—O—$CH_2$— 4H).
Figure 2:
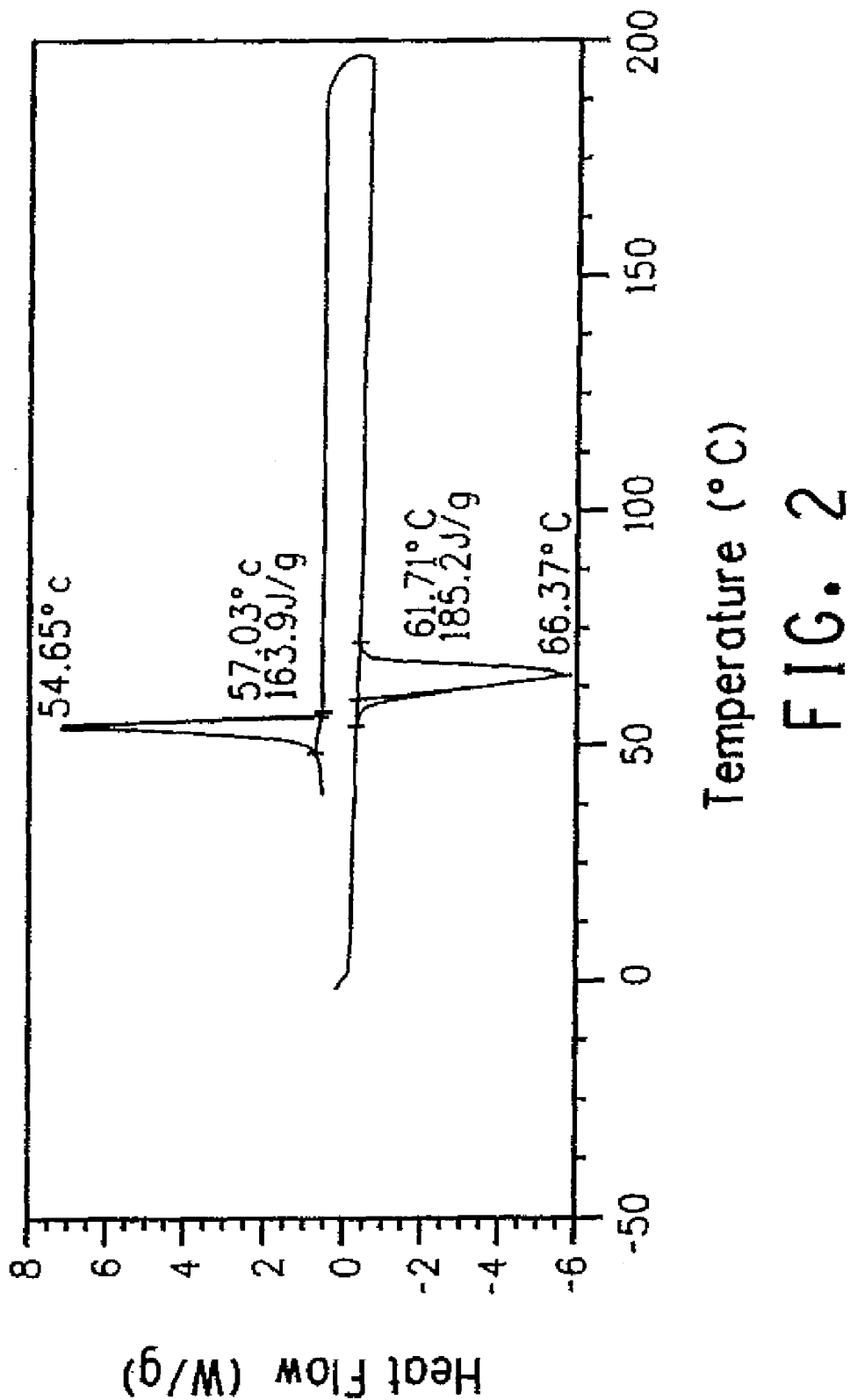
FIG. 2 is a DSC (Differential Scanning Calorimetry) curve of the product obtained in Example 3. DSC (Tm=66.4° C. and Tc=54.7° C.).

The transformed *E. coli* DH5α containing cosmid pKP1 containing a portion of the *Klebsiella* genome encoding the glycerol dehydratase enzyme was deposited on 18 Apr. 1995 with the ATCC under the terms of the Budapest Treaty and is identified by the ATCC number ATCC 69789. The transformed *E. coli* DH5α containing cosmid pKP4 containing a portion of the *Klebsiella* genome encoding a diol dehydratase enzyme was deposited on 18 Apr. 1995 with the ATCC under the terms of the Budapest Treaty and is identified by the ATCC number ATCC 69790. As used herein, "ATCC" refers to the American Type Culture Collection international depository located at 10801 University Boulevard, Manassas, Va., 20110-2209, U.S.A. The "ATCC No." is the accession number to cultures on deposit with the ATCC.

DETAILED DESCRIPTION OF THE INVENTION

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Conjugate esters of 1,3-propanediol are suitable, in a non-limiting way, for use in personal compositions such as liquid hand soaps, shampoos and body detergents as emulsifiers, pearlizing agents, surfactants, gelling agents, structurants, thickeners, and opacifiers. The esters described herein are especially desirable as components of liquid soap, shampoo, and body detergent formulations as they provide the intended functionality and can be produced from a biologically-derived compound.

The esters of 1,3-propanediol are also useful as an active ingredient in personal care products and cosmetics as emollients. In other applications such esters are useful in the delivery, application, or effectiveness of the personal care product and cosmetic. The esters act as an additive or adjuvant when used to improve the delivery, application or effectiveness of a product. Specifically, in a non-limiting way, the esters can be used as a humectant, opacifier, pearlizing agent, gelling agent, emulsifier, surfactant, structurant, thickener, compatibilizer or solvent for cosmetics and personal care products.

Fatty acid monoesters and diesters of biologically-produced 1,3 propanediol are formed by esterification of biologically derived 1,3-propanediol. Biologically-derived 1,3-propanediol can be obtained through catalytic conversion of non-fossil fuel carbon via fermentation with an organism that is able to synthesize 1,3-propanediol. The process provides 1,3-propanediol and its conjugate monoesters and diesters without introducing additional carbon into the atmosphere during the production, use, or disposal of the material.

Biologically produced 1,3 propanediol represents a new feedstock for useful monoesters and diesters of 1,3 propanediol. Such monoesters and diesters have not previously been produced from a biosourced monomer. As such, new compositions of matter, comprising 1,3 propanediol esters derived from biosourced carbon substrates are provided.

These compositions may be distinguished from similar compositions derived from all petrochemical carbon on the basis of biobased carbon content.

The terms used in this application shall be accorded the following definitions:

The terms "bio-PDO esters", "bio-based PDO ester", "biologically-derived-PDO esters" and "biologically-based 1,3-propanediol esters" and similar terms as used herein refer to monoesters and diesters produced from biologically produced 1,3-propanediol.

The terms "bioPDO", "bio-produced PDO", "biologically-produced 1,3-propanediol", "bio-derived 1,3-propanediol" and "biologically derived 1,3-propanediol" and similar terms as used here in refer to 1,3-propanediol derived from microorganism metabolism of plant-derived sugars composed of carbon of atmospheric origin, and not composed of fossil-fuel carbon.

"Substantially purified," as used by applicants to describe the biologically-produced 1,3-propanediol produced by the process of the invention, denotes a composition comprising 1,3-propanediol having at least one of the following characteristics: 1) an ultraviolet absorption at 220 nm of less than about 0.200 and at 250 nm of less than about 0.075 and at 275 nm of less than about 0.075; or 2) a composition having L*a*b* "b*" color value of less than about 0.15 and an absorbance at 270 nm of less than about 0.075; or 3) a peroxide composition of less than about 10 ppm; or 4) a concentration of total organic impurities of less than about 400 ppm.

A "b*" value is the spectrophotometrically determined "Yellow Blue measurement as defined by the CIE L*a*b* measurement ASTM D6290.

The abbreviation "AMS" refers to accelerator mass spectrometry.

"Biologically produced" means organic compounds produced by one or more species or strains of living organisms, including particularly strains of bacteria, yeast, fungus and other microbes. "Bio-produced" and biologically produced are used synonymously herein. Such organic compounds are composed of carbon from atmospheric carbon dioxide converted to sugars and starches by green plants.

"Biologically-based" means that the organic compound is synthesized from biologically produced organic components. It is further contemplated that the synthesis process disclosed herein is capable of effectively synthesizing other monoesters and diesters from bio-produced alcohols other than 1,3-propanediol; particularly including ethylene glycol, diethylene glycol, triethylene glycol, 1,2-propylene glycol, dipropylene diol, tripropylene diol, 2-methyl 1,3-propanediol, neopentyl glycol and bisphenol A. "Bio-based", and "bio-sourced"; "biologically derived"; and "bio-derived" are used synonymously herein.

"Fermentation" as used refers to the process of metabolizing simple sugars into other organic compounds. As used herein fermentation specifically refers to the metabolism of plant derived sugars, such sugar are composed of carbon of atmospheric origin.

"Carbon of atmospheric origin" as used herein refers to carbon atoms from carbon dioxide molecules that have recently, in the last few decades, been free in the earth's atmosphere. Such carbons in mass are identifiable by the present of particular radioisotopes as described herein. "Green carbon", "atmospheric carbon", "environmentally friendly carbon", "life-cycle carbon", "non-fossil fuel based carbon", "non-petroleum based carbon", "carbon of atmospheric origin", and "biobased carbon" are used synonymously herein.

"Carbon of fossil origin" as used herein refers to carbon of petrochemical origin. Such carbon has not been exposed to UV rays as atmospheric carbon has, therefore masses of carbon of fossil origin has few radioisotopes in their population. Carbon of fossil origin is identifiable by means described herein. "Fossil fuel carbon", "fossil carbon", "polluting carbon", "petrochemical carbon", "petro-carbon" and carbon of fossil origin are used synonymously herein.

"Naturally occurring" as used herein refers to substances that are derived from a renewable source and/or are produced by a biologically-based process.

"Fatty acid" as used herein refers to carboxylic acids that are often have long aliphatic tails, however, carboxylic acids of carbon length 1-40 are specifically included in this definition for the purpose of describing the present invention. "Fatty acid esters" as used herein are esters, which are composed of such, defined fatty acids.

"Catalyst" as used herein refers to a substance that is facilitates a chemical reaction without being either a reactant or a product of said reaction.

By the acronym "NMR" is meant nuclear magnetic resonance.

By the terms "color" and "color bodies" is meant the existence of visible color that can be quantified using a spectrocolorimeter in the range of visible light, using wavelengths of approximately 400-800 nm, and by comparison with pure water. Reaction conditions can have an important effect on the nature of color production. Examples of relevant conditions include the temperatures used, the catalyst and amount of catalyst. While not wishing to be bound by theory, we believe color precursors include trace amounts of impurities comprising olefinic bonds, acetals and other carbonyl compounds, peroxides, etc. At least some of these impurities may be detected by such methods as UV spectroscopy, or peroxide titration.

"Color index" refers to an analytic measure of the electromagnetic radiation-absorbing properties of a substance or compound.

"Hydrogenation reactor" refers to any of the known chemical reactors known in the literature, including but not limited to shaker-tubes, batch autoclaves, slurry reactors, up-flow packed bed, and trickle flow packed bed reactors.

The abbreviation "IRMS" refers to measurements of CO2 by high precision stable isotope ratio mass spectrometry.

The term "carbon substrate" means any carbon source capable of being metabolized by a microorganism wherein the substrate contains at least one carbon atom.

The term "shampoo" as used herein means a composition for cleansing and conditioning hair or skin, including scalp, face, and body.

The term "personal care composition" as used herein refers to a substance that is in grooming. These personal care compositions include, but are not limited to, skin care compositions, skin cleansing compositions, make-up, facial lotions, cream moisturizers, body washes, body lotions, liquid soap, milk bath, bronzing sticks, foot creams, hand creams, lipstick, eyeshadow, foundation, facial powders, deodorant, shaving cream compositions, nail polishes, shaving lotions, cream depilatories, lotion depilatories, facial masks made with clay materials, anti-aging products, baby shampoos, hair reconstructionors, hair conditioners, hair treatment creams, styling gels, styling foams, hair mousses, hair sprays, set lotions, blow-styling lotions, hair color lotions, and hair relaxing compositions. Personal care products could be used on any animal. The present invention is preferred to be used in the grooming of mammals and birds. The present invention is more preferred to be use in the grooming of humans, canines, felines, and equines. The present invention is most preferred to be used in the grooming of humans. "Personal care product" and personal care composition are used synonymously herein.

Unless otherwise stated, all percentages, parts, ratios, etc., are by weight. Trademarks are shown in upper case. Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed.

A small amount of the carbon dioxide in the atmosphere is radioactive. This 14C carbon dioxide is created when nitrogen is struck by an ultra-violet light produced neutron, causing the nitrogen to lose a proton and form carbon of molecular weight 14 which is immediately oxidized in carbon dioxide. This radioactive isotope represents a small but measurable fraction of atmospheric carbon. Atmospheric carbon dioxide is cycled by green plants to make organic molecules during the process known as photosynthesis. The cycle is completed when the green plants or other forms of life metabolize the organic molecules producing carbon dioxide which is released back to the atmosphere. Virtually all forms of life on Earth depend on this green plant production of organic molecule to produce the chemical energy that facilitates growth and reproduction. Therefore, the 14C that exists in the atmosphere becomes part of all life forms, and their biological products. These renewably based organic molecules that biodegrade to CO2 do not contribute to global warming as there is no net increase of carbon emitted to the atmosphere. In contrast, fossil fuel based carbon does not have the signature radiocarbon ratio of atmospheric carbon dioxide.

Assessment of the renewably based carbon in a material can be performed through standard test methods. Using radiocarbon and isotope ratio mass spectrometry analysis, the biobased content of materials can be determined. ASTM International, formally known as the American Society for Testing and Materials, has established a standard method for assessing the biobased content of materials. The ASTM method is designated ASTM-D6866.

The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon). If the material being analyzed is a mixture of present day radiocarbon and fossil carbon (containing no radiocarbon), then the pMC value obtained correlates directly to the amount of Biomass material present in the sample.

The modern reference standard used in radiocarbon dating is a NIST (National Institute of Standards and Technology) standard with a known radiocarbon content equivalent approximately to the year AD 1950. AD 1950 was chosen since it represented a time prior to thermo-nuclear weapons testing which introduced large amounts of excess radiocarbon into the atmosphere with each explosion (termed "bomb carbon"). The AD 1950 reference represents 100 pMC.

"Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. It's gradually decreased over time with today's value being near 107.5 pMC. This means that a fresh biomass material such as corn could give a radiocarbon signature near 107.5 pMC.

Combining fossil carbon with present day carbon into a material will result in a dilution of the present day pMC content. By presuming 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, it would give a radiocarbon signature near 54 pMC.

A biomass content result is derived by assigning 100% equal to 107.5 pMC and 0% equal to 0 pMC. In this regard, a sample measuring 99 pMC will give an equivalent biobased content result of 93%.

Assessment of the materials described herein were done in accordance with ASTM-D6866. The mean values quoted in this report encompasses an absolute range of 6% (plus and minus 3% on either side of the biobased content value) to account for variations in end-component radiocarbon signatures. It is presumed that all materials are present day or fossil in origin and that the desired result is the amount of biobased component "present" in the material, not the amount of biobased material "used" in the manufacturing process.

Compositions in accordance with the invention include a composition comprising an ester of 1,3-propanediol. The esters can have a varying amount of biobased carbon depending on the compound used in the esterification. Biologically derived 1,3-propanediol contains biobased carbon. All three carbon atoms in 1,3 propanediol are biobased carbons. If the conjugate esters are formed using carboxylic acids that contain all biobased carbon, then the resulting esters also contain all biobased carbon. If, however, the carboxylic acids contain non-biobased carbons, i.e. carbons from a fossil fuel source, then the resulting ester will contain a percentage of biobased carbon in proportion to the number of carbons contributed from the carboxylic acid compared to the three carbons contributed from the biologically-derived 1,3-propanediol.

For example, distearate propanediol contains 39 carbon atoms, 18 from each of the stearic acid carbon chains and three from the 1,3-propanediol. Accordingly, if the strearic acid is non-biobased, 36 carbons out of the total 39 in distearate propanediol are non-biobased carbon. The predicted theoretical biobased content of distearate propanediol made from biologically-derived propanediol, and non-biologically derived strearic acid is approximately 7.7 percent.

In an analysis performed using the ASTM-D6866 method, propylene glycol dibenzoate (BENZOFLEX® 284, Velsicol Chem. Corp. Rosemont, Ill.) was found to have 0% bio-based carbon content. The same analysis of propanediol dibenzoate, synthesized using biologically-derived 1,3-propanediol had 19% bio-based carbon content. The predicted bio-based carbon content propanediol dibenzoate made from biologically-derived 1,3 propanediol is 17.6%, which is within the standard deviation of the method.

If the stearic acid in the above example is biobased, the resulting distearate propanediol would have a biobased content of 100%. Accordingly, the conjugate esters of biologically-derived 1,3-propanediol have biobased content values proportional to the biobased content of the acids used to form the esters. The esters therefore can have biobased content of at least 3% biobased carbon, at least 6% biobased carbon, at least 10% biobased carbon, at least 25% biobased carbon, at least 50% biobased carbon, at least 75% biobased carbon, and 100% biobased carbon.

If the organic acid is steric acid or oleic acid, the ester recovered should be greater than 5% biobased carbon. When the organic acid is lauric acid, the ester recovered should be greater than 10% biobased carbon.

Biologically-Derived 1,3-propanediol

Biologically-derived 1,3-propanediol is collected in a high purity form. Such 1,3-propanediol has at least one of the following characteristics: 1) an ultraviolet absorption at 220 nm of less than about 0.200 and at 250 nm of less than about 0.075 and at 275 nm of less than about 0.075; or 2) a composition having L*a*b* "b*" color value of less than about 0.15 and an absorbance at 270 nm of less than about 0.075; or 3) a peroxide composition of less than about 10 ppm; or 4) a concentration of total organic impurities of less than about 400 ppm. A "b*" value is the spectrophotometrically determined Yellow Blue measurement as defined by the CIE L*a*b* measurement ASTM D6290.

The level of 1,3-propanediol purity can be characterized in a number of different ways. For example, measuring the remaining levels of contaminating organic impurities is one useful measure. Biologically-derived 1,3-propanediol can have a purity level of less than about 400 ppm total organic contaminants; preferably less than about 300 ppm; and most preferably less than about 150 ppm. The term ppm total organic purity refers to parts per million levels of carbon-containing compounds (other than 1,3-propanediol) as measured by gas chromatography.

Biologically-derived 1,3-propanediol can also be characterized using a number of other parameters, such as ultraviolet light absorbance at varying wavelengths. The wavelengths 220 nm, 240 nm and 270 nm have been found to be useful in determining purity levels of the composition. Biologically-derived 1,3-propanediol can have a purity level wherein the UV absorption at 220 nm is less than about 0.200 and at 240 nm is less than about 0.075 and at 270 nm is less than about 0.075.

Biologically-derived 1,3-propanediol can have a b* color value (CIE L*a*b*) of less than about 0.15.

The purity of biologically-derived 1,3-propanediol compositions can also be assessed in a meaningful way by measuring levels of peroxide. Biologically-derived 1,3-propanediol can have a concentration of peroxide of less than about 10 ppm.

It is believed that the aforementioned purity level parameters for biologically-derived and purified 1,3-propanediol (using methods similar or comparable to those disclosed in U.S. Patent Application No. 2005/0069997) distinguishes such compositions from 1,3-propanediol compositions prepared from chemically purified 1,3-propanediol derived from petroleum sources.

1,3-propanediol produced biologically via fermentation is known, including in U.S. Pat. Nos. 5,686,276, 6,358,716, and 6,136,576, which disclose a process using a recombinantly-engineered bacteria that is able to synthesize 1,3-propanediol during fermentation using inexpensive green carbon sources such as glucose or other sugars from plants. These patents are specifically incorporated herein by reference. Biologically-derived 1,3-propanediol can be obtained based upon use of the fermentation broth generated by a genetically-engineered *Escherichia coli* (*E. coli*), as disclosed in U.S. Pat. No. 5,686,276. Other single organisms, or combinations of organisms, may also be used to biologically produce 1,3-propanediol, using organisms that have been genetically-engineered according to methods known in the art. "Fermentation" refers to a system that catalyzes a reaction between substrate(s) and other nutrients to product(s) through use of a biocatalyst. The biocatalysts can be a whole organism, an isolated enzyme, or any combination or component thereof that is enzymatically active. Fermentation systems useful for producing and purifying biologically-derived 1,3-propanediol are disclosed in, for example, Published U.S. Patent Application No. 2005/0069997 incorporated herein by reference.

Biologically derived 1,3-propanediol contains carbon from the atmosphere incorporated by plants, which compose the feedstock for the production of biologically derived 1,3-propanediol. In this way, the biologically derived 1,3-propanediol contains only renewable carbon, and not fossil fuel based, or petroleum based carbon. Therefore the use of biologically derived 1,3-propanediol and its conjugate esters has less impact on the environment as the 1,3-propanediol does not deplete diminishing fossil fuels. The use of biologically derived 1,3-propanediol and its conjugate esters also does not make a net addition of carbon dioxide to the atmosphere, and thus does not contribute to greenhouse gas emissions. Accordingly, the present invention can be characterized as more natural and having less environmental impact than similar compositions comprising petroleum based glycols.

Moreover, as the purity of the biologically derived 1,3-propanediol utilized in the food compositions described herein is higher than chemically synthesized pdo and other glycols, risk of introducing impurities that may be unacceptable in food applications is reduced by its use over commonly used glycols, such as propylene glycol.

In one embodiment of the invention, a composition comprising 1,3-propanediol and an ester of 1,3-propanediol is provided, where the 1,3-propanediol is biologically derived. The biologically-derived 1,3-propanediol in these compositions can have at least 85% biobased carbon, at least 95% biobased carbon, or 100% biobased carbon, when assessed by the application of ASTM-D6866 as described above.

A sample of biologically-derived 1,3-propanediol was analyzed using ASTM method D 6866-05. The results received from Iowa State University demonstrated that the above sample was 100% bio-based content. In a separate analysis, also performed using a ASTM-D6866 method, chemical, or petroleum-based 1,3-propanediol (purchased from SHELL) was found to have 0% bio-based content. Propylene glycol (USP grade from ALDRICH) was found to have 0% bio-based content.

It is contemplated herein that other renewably-based or biologically-derived glycols, such as ethylene glycol or 1,2 propylene glycol, diethylene glycol, triethylene glycol among others, can be used in the personal care compositions of the present invention.

There may be certain instances wherein a personal care compositions composition of the invention may comprise a combination of a biologically-derived 1,3-propanediol and one or more non biologically-derived glycol components, such as, for example, chemically synthesized 1,3-propanediol. In such occasions, it may be difficult, if not impossible to determine which percentage of the glycol composition is biologically-derived, other than by calculating the bio-based carbon content of the glycol component. In this regard, in the personal care compositions of the invention, the 1,3-propanediol use to form 1,3 propanediol esters, can comprise at least about 1% bio-based carbon content up to 100% bio-based carbon content, and any percentage there between.

Ester Conjugates of Biologically Derived 1,3-Propanediol

Esters of biologically derived 1,3-propanediol, "bio-PDO" can be synthesized by contacting biologically derived 1,3-propanediol with an organic acid. The organic acid can be from any origin, preferably either a biosource or synthesized from a fossil source. Most preferably the organic acid is derived from natural sources or bio-derived having formula R1-COOH. Where in the substituent R1 can be saturated or unsaturated, substituted or unsubstituted, aliphatic or aromatic, linear or branched hydrocarbon having chain length 1 to 40 or their salts or alkyl esters. The hydrocarbon chain can also have one or more functional groups such as alkene, amide, amine, carbonyl, carboxylic acid, halide, hydroxyl groups. Naturally occurring organic acids produced esters containing all biobased carbon. These naturally occurring organic acids, especially those produced by a biological organism, are classified as bio-produced and the resulting ester or diester could thereby also be classified as bio-produced. Naturally occurring sources of such fatty acids include coconut oil, various animal tallows, lanolin, fish oil, beeswax, palm oil, peanut oil, olive oil, cottonseed oil, soybean oil, corn oil, rape seed oil. Conventional fractionation and/or hydrolysis techniques can be used if necessary to obtain the fatty acids from such materials.

Appropriate carboxylic acids for producing esters of biologically-derived 1,3-propanediol generally include: (1) C1-C3 carbon containing mono carboxylic acids, including formic acid and acetic acid; (2) fatty acids, such as those acids containing four or more carbon atoms; (3) saturated fatty acids, such as butyric acid, caproic acid, valeric acid, caprylic acid, capric acid, lauric acid, myristic acid, palmitic acid, stearic acid, arachidic acid, and behenic acid; (4) unsaturated fatty acids, such as oleic acid, linoleic acid, and euricic acid; (5) polyunsaturated fatty acids, such as alpha-linolenic acid, stearidonic acid (or moroctic acid), eicosatetraenoic acid, omega-6 fatty acids, arachidonic acids, and omega-3 fatty acids, eicosapentaenoic acid (or timnodonic acid), dosocapentaenoic acid (or clupanodonic acid), and docosahexaenoic acid (or cervonic acid); (6) hydroxy fatty acids, such as 2-hydroxy linoleic acid, and recinoleic acid; phenylalkanoic fatty acids, such as 11-phenyl undecanoic acid, 13-phenyl tridecanoid acid, and 15-phenyl tridecanoid acid; and (7) cyclohexyl fatty acids, such as 11-cyclohexyl undecanoic acid, and 13-cyclohexyl tridecanoic acid.

The following acids and their salts or alkyl esters are specifically useful, acetic, alginic, butyric, lauric, myristic, palmitic, stearic, arachidic, adipic, benzoic, caprylic, maleic, palmitic, sebacic, archidonic, erucic, palmitoleic, pentadecanoic, heptadecanoic, nondecanoic, octadectetraenoic, eicosatetraenoic, eicosapentaenoic, docasapentaenoic, tetracosapentaenoic, tetrahexaenoic, docosahexenoic, (alpha)-linolenic, docosahexaenoic, eicosapentaenoic, linoleic, arachidonic, oleic, erucic, formic, propionic, valeric, caproic, capric, malonic, succinic, glutaric, adipic, pimelic, suberic, azelaic, tartaric, citric, salicylic, acetylsalicylic, pelargonic, behenic, cerotic, margaric, montanic, melissic, lacceroic, ceromelissic, geddic, ceroplastic undecylenic, ricinoleic, and elaeostearic acid as well as mixtures of such acids. A more preferred list of suitable organic acids are acetic, adipic, benzoic, maleic, sebacic, and mixtures of such acids. A more preferred list of suitable "fatty acids" meaning generally acids named containing 8-40 carbon in the carbon useful in the present invention include butyric, valeric, caproic, caprylic, pelargonic, capric, lauric, myristic, palmitic, stearic, arachidic, behenic, cerotic, oleic, linoleic, linolenic, margaric, montanic, melissic, lacceroic, ceromelissic, geddic, ceroplastic and the mixtures of such acids. Among those acids, these acids, and their salts and alkyl esters are most preferred stearic, lauric, palmetic, oleic, 2-ethyl hexanoic, and 12-hydroxystearic and mixtures of such acids.

The esters produced include all the appropriate conjugate mono and diesters of 1,3 propanediol using the described organic acids. Some esters in particular that are produced include propanediol distearate and monostearate, propanediol dilaurate and monolaurate, propanediol dioleate and monooleate, propanediol divalerate and monovalerate, propanediol dicaprylate and monocaprylate, propanediol dimyristate and monomyristate, propanediol dipalmitate and monopalmitate, propanediol dibehenate and monobehenate, propanediol adipate, propanediol maleate, propanediol dibenzoate, propanediol diacetate, and all mixtures thereof.

In particular, the esters produced include: propanediol distearate and monostearate, propanediol dioleate and monooleate, propanediol dicaprylate and monocaprylate, propanediol dimyristate and monomyristate, and all mixtures thereof.

Generally 1,3-propanediol can be contacted, preferably in the presence of an inert gas reacted with a fatty acid or mixture of fatty acids or salts of fatty acids in the absence or presence of a catalyst or mixture of two or more catalysts, at temperatures ranging from 25° C. to 400° C.

During the contacting, water is formed and can be removed in the inert gas stream or under vacuum to drive the reaction complete. Any volatile byproducts can be removed similarly. When the reaction is complete, the heating can be stopped and cooled.

The catalyst can be removed preferably by dissolving and removing in deionized water. If catalyst can be removed by treating with deionized water, the reaction mixture is treated with aqueous solutions of acid or base to forms salts and removing the salts either by washing or filtering.

Further purification to obtain high purity fatty esters, preferably for pharmaceutical application can be carried out by dissolving in a solvent that dissolves fatty ester easily at higher temperatures and least at lower temperatures and recrystallyzing with or without addition of additional solvent at low temperatures.

The catalyst can be an acid for non-limiting examples, sulfuric acid, or p-toluene sulfonic acid. The catalyst can also be a base, for non-limiting example, sodium hydroxide. The catalyst can also be a salt, for non-limiting example, potassium acetate. The catalyst can also be an alkoxide, for non-limiting example, titanium tetraisopropoxide. The catalyst can also be a heterogeneous catalyst, for non-limiting examples: zeolite, heteropolyacid, amberlyst, or ion exchange resin. The catalyst can also be a metal salt, for non-limiting examples, tin chloride, or copper chloride. The catalyst can also be an enzyme, such as those known in the art. The catalyst can also be an organic acid, for a non-limiting example, formic acid. Finally the catalyst can also be an organometalic compound, for non-limiting example, n-butylstannoic acid.

This process can be carried out in the presence or absence of a solvent. If a solvent is not necessary to facilitate the production of fatty ester, it is preferred that the process is carried out in the absence of solvent.

The process can be carried out at atmospheric pressure or under vacuum or under pressurized conditions.

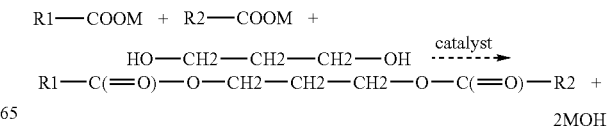

Where R1 and R2 is a hydrocarbon, preferably with a carbon chain length of about 1 to about 40. Such hydrocarbons can be saturated or unsaturated, substituted or unsubstituted, linear or branched M is hydrogen, an alkali metal or an alkyl group.

Reaction 2 (monoester)

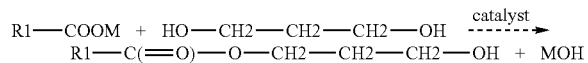

R1—COOM + HO—CH2—CH2—CH2—OH $\xrightarrow{\text{catalyst}}$
R1—C(=O)—O—CH2—CH2—CH2—OH + MOH Where R1 is a hydrocarbon, preferably with a carbon chain length of about 1 to about 40. Such hydrocarbons can be saturated or unsaturated, substituted or unsubstituted, linear or branched. M is hydrogen, an alkali metal or an alkyl group.

Compositions in accordance with the invention comprise esters in which R1 has one or more functional groups selected from the group consisting of alkene, amide, amine, carbonyl, carboxylic acid, halide, hydroxyl groups, ether, alkyl ether, sulfate and ethersulfate. The esters can have the formula R1-C(=O)—O—CH2-CH2-CH2-O—C(=O)—R2, wherein both R1 and R2 are linear or branched carbon chains of a length between about 1 an about 40 carbons. R1 and R2 can have one or more functional groups selected from the group consisting of alkene, amide, amine, carbonyl, carboxylic acid, halide, hydroxyl groups, ether, alkyl ether, sulfate and ethersulfate. Additionally, R1 and R2 can be the same carbon chain in the case of a diester.

Any molar ratio of diol to dicarboxylic acid or its salt or its ester can be used. The preferred range of the diol to dicarboxylic acid is from about 1:3 to about 2:1. This ratio can be adjusted to shift the favor of the reaction from monoester production to diester production. Generally, to favor the production of diesters slightly more than about a 1:2 ratio is used; whereas to favor the production of monoesters about a 1.1 ratio is used. In general, if the diester product is desired over the monoester the ratio of diol to dicarboxylic acid can range from about 1.01:2 to about 1.1:2; however if the monoester is desired a range of ratios from about 1.01:1 to about 2:1 is used.

The catalyst content for the reaction can be from 1 ppm to 60 wt % of the reaction mixture, preferably from 10 ppm to 10 wt %, more preferably from 50 ppm to 2 wt % of the reaction mixture.

The product may contain diesters, monoesters or combination diesters and monoesters and small percentage of unreacted acid and diol depending on the reaction conditions. Unreacted diol can be removed by washing with deionized water. Unreacted acid can be removed by washing with deionized water or aqueous solutions having base or during recrystallization.

Any ester of 1,3-propanediol can be made or used in accordance with the present invention. Short, middle and long chain monoesters and diesters of the 1,3-propanediol can be made. Specifically those acids containing between about 1 and about 36 carbons in the alkyl chain can be produced. More specifically, the following monoesters and diesters can be produced: propanediol distearate (monostearate and the mixture), propandiol dilaurate (monolaurate and the mixture), propanediol dioleate (monooleate and the mixture), propanediol divalerate (monovalerate and the mixture), propanediol dicaprylate (monocaprylate and the mixture), propanediol dimyristate (monomyristate and the mixture), propanediol dipalmitate (monopalmitate and the mixture), propanediol dibehenate (monobehenate and the mixture), propanediol adipate, propanediol maleate, propanediol dibenzoate, and propanediol diacetate.

Compositions comprising an ester of 1,3-propanediol, wherein the 1,3-propanediol is biologically derived contain biobased carbon from the biologically derived 1,3-propanediol. Accordingly, these esters can have varying amounts of biobased carbon, depending on what acids are used in the esterification process. The compositions can include esters that have at least 1% biobased carbon, at least 3% biobased carbon, at least 6% biobased carbon, at least 10% biobased carbon, at least 25% biobased carbon, at least 50% biobased carbon, at least 75% biobased carbon, or 100% biobased carbon depending on the length of the carbon chain of the organic acid used to produce the ester, whether the ester is a diester or a monoester, and whether the organic acid contained biobased carbon or fossil-fuel based carbon.

These compositions comprising an ester of 1,3-propanediol can be produced by providing biologically produced 1,3-propanediol; contacting the 1,3-propanediol with an organic acid, wherein the ester is produced; and recovering the ester. The 1,3-propanediol provided can have at least 90% biobased carbon, at least 95% biobased carbon, or 100% biobased carbon. Additionally, the biologically-produced 1,3-propanediol provided for the process can have at least one of the following characteristics: 1) an ultraviolet absorption of less than about 0.200 at 220 nm and less than about 0.075 at 250 nm and less than about 0.075 at 275 nm; 2) a composition having L*a*b* "b*" color value of less than about 0.15 and an absorbance of less than about 0.075 at 270 nm; 3) a peroxide composition of less than about 10 ppm; and 4) a concentration of total organic impurities of less than about 400 ppm.

The ester can also be produced by providing 1,3-propanediol with at least 90% biobased carbon; contacting the 1,3-propanediol with an acid, forming the ester; and recovering the ester. The contacting of the 1,3-propanediol with an acid can be done in the presence of a catalyst to facilitate the esterification reaction, and the catalyst can be categorized as a member of one or more of the acids, bases, salts, alkoxides, heterogeneous, catalysts, metal salts, enzymes, organic acids, and organometalic compounds. Specifically, the catalyst can be sulfuric acid, or p-toluene sulfonic acid, sodium hydroxide, potassium acetate, titanium tetraisopropoxide, zeolite, heteropolyacid, amberlyst, ion exchange resin, tin chloride, or copper chloride, formic acid, or n-butylstannoic acid.

Uses of Esters from Bio-Derived 1,3-propanediol in Personal Care Products

The monoesters and diesters of bio-derived 1,3-propanediol are useful in a variety of applications. The esters are suitable for use as an emulsifier, a pearlizing agent, a surfactant, a gelling agent, a structurant, a thickener, an opacifier, an emollient, an additive, an adjuvant, a humectant, a compatibilizer, and a solvent for cosmetics and personal care products.

Such esters are also useful as a solvent for botanical products. Such botanical products include, but are not limited to, all plants, their seeds, stems, roots, flowers, leaves, pollen, spices, oils and botanical extracts generally. As a solvent to botanicals, the esters can be used to incorporate the botanicals into personal care and cosmetic products. Esters as described herein can also be used in inks as an emulsifier in cosmetic inks like tattoos or henna dyes. Such esters are useful in preparation of solid or near solid personal care products such as stick deodorants, bronzing sticks, and lipsticks.

In one embodiment of the invention. a personal care composition comprising an ester of 1,3-propanediol and an acceptable carrier is provided. While the personal care compositions can include synthetic materials, they are the 1,3 propanediol esters derived from biologically-derived 1,3-propanediol are compatible with natural ingredients, or essentially natural ingredients in forming natural personal care products.

The compositions include formulations for skin care, skin cleansing, make-up, facial lotion, moisturizer, body wash, body lotion, foot care formulation, hand cream, lipstick, lip gloss, lip pencil, eye shadow, gel eye color, eye liner, eye pencil, mascara, concealer, foundation, facial powder, liquid rouges, blush, deodorant, antiperspirant, shaving cream, shaving lotion, nail polish, gel polish removers, cuticle remover, cuticle cream, acne cream, acne cleansing scrub, toothpaste, depilatory formulation, facial mask, anti-aging formulation, shampoo, hair conditioner, hair treatment formulation, hair reconstructioner, styling gel, styling foam, hair mousse, hair spray, hair set lotion, blow-styling lotion, hair color lotion and dyes, hair bleaching cream, hair relaxing, curl activator, fragrant hair gloss, sun care formulations like sun stick and sun screen, sunless tanner, bronzing stick, soap, hand sanitizer, antibacterial hand cleaner, body scrub, hand scrub, bubble bath, bath oils, baby lotion, diaper rash cream, wet wipe, baby bath, and vitamin cream.

In forming these personal care compositions, it may be desirable to include a variety of ingredients to achieve specific properties. Appropriate ingredients for the personal care compositions of the invention include, among others: conditioning agents, moisturizing agents, emollients, astringents, antiperspirant compounds, biocidal compounds, sunscreens, UV absorbers, pigments, fragrances, actives, anti-aging agents, enzymes, proteins, vitamins, or mixtures thereof.

The compositions of the present invention preferably comprise a safe and effective amount of a cosmetically acceptable carrier, suitable for topical application to the skin within which the essential materials and optional other materials are incorporated to enable the essential materials and optional components to be delivered to the skin at an appropriate concentration. The carrier can thus act as a diluent, dispersant, solvent, or the like for any active ingredients which ensures that they can be applied to, and distributed evenly over, the selected target at an appropriate concentration.

The type of carrier utilized in the personal care compositions depends on the types of product form desired for the composition. The topical compositions can be made into a wide variety of product forms such as are known in the art. These include but are not limited to, lotions, creams, gels, sticks, sprays, ointments, pastes and mousses. These product forms may comprise several types of carriers including, but not limited to, solutions, aerosols, emulsions, gels, solids and liposomes.

The personal care compositions can have between about 0.5% and about 2% weight ester, between about 2% and about 5% weight ester, between about 5% and about 10% weight ester, between about 10% and about 20% weight ester, between about 20% and about 50% weight ester, or between about 50% and about 80% weight ester, depending on the formulation used.

In another embodiment of the invention, the personal care compositions can include a glycol component. The glycol component can be 1,3-propanediol. Preferably, when 1,3 propanediol is used as the glycol component, it will be biologically-derived 1,3-propanediol. This biologically-derived 1,3-propanediol can have at least 90% biobased carbon content. Preferably, the 1,3-propanediol has at least 95% biobased carbon content, and more preferably has 100% biobased carbon content.

The personal care compositions can be intended for grooming mammals or avians. More specifically, the personal care compositions can be intended for grooming humans, canines, felines, or equines.

In still another embodiment of the invention, a process for producing a personal care composition with an ester of 1,3-propanediol and an acceptable carrier is provided. The process of making the composition includes providing biologically produced 1,3-propanediol and contacting the 1,3-propanediol with an organic acid. This produces the ester. The process includes recovering the ester and incorporating the ester into a personal care formulation.

In yet another embodiment, a process for producing a personal care composition is provided that includes providing an ester of 1,3-propanediol and incorporating the ester into a personal care formulation.

The personal care compositions preferably include a safe and effective amount of a dermatologically or cosmetically acceptable carrier, suitable for topical application to the skin within which the essential materials and optional other materials are incorporated to enable the essential materials and optional components to be delivered to the skin at an appropriate concentration. The carrier can thus act as a diluent, dispersant, solvent, or the like for any active ingredients which ensures that they can be applied to, and distributed evenly over, the selected target at an appropriate concentration.

The type of carrier used in the personal care compositions depends on the types of product form desired for the composition. The topical compositions useful in the subject invention may be made into a wide variety of product forms such as are known in the art. These include but are not limited to, lotions, creams, gels, sticks, sprays, ointments, pastes and mousses. These product forms may comprise several types of carriers including, but not limited to, solutions, aerosols, emulsions, gels, solids and liposomes.

For purposes of this application, that the words "personal care" and "cosmetics", while used separately at times, are used interchangeably throughout the application to describe the compositions of this invention. Accordingly, the term "personal care compositions" embraces both personal care product formulations and cosmetic formulations.

Esters of 1,3 propanediol can be present in the aforementioned personal care and cosmetics compositions in varying amounts depending on the type of formulation.

Baby products, such as, for example, baby shampoos, soaps, wipes, lotions, oils, powders, and creams, can have a 1,3 propanediol ester concentration ranging between about 0.1% to about 25% by weight, and preferably between about 10% to about 10% by weight, and more preferably 1 to 5%.

Bath preparations such as, for example, bath oils, tablets, and salts; bubble baths and bath capsules, can have a 1,3 propanediol ester concentration ranging between about 0.001% to about 50%, and preferably from about 0.1% to about 10%, and more preferably from about 1% to about 5%.

Eye makeup preparations such as, for example, eyebrow pencil; eyeliner; eye shadow; eye lotion; eye makeup remover; and mascara, can have a 1,3 propanediol ester concentration ranging between about 0.001% to about 75%, preferably 0.01% to about 25%, and more preferably, 0.05% to about 5%.

Fragrance preparations such as, for example, colognes and toilet waters; perfumes; powders (dusting and talcum) (excluding aftershave talc); and sachets, can have a 1,3 propanediol ester concentration ranging between about 0.001% to about 99%, preferably from about 0.01% to about 10%, and more preferably from about 0.05% to about 5%.

Hair preparations (noncoloring) such as, for example, hair conditioners; hair sprays (aerosol fixatives); hair straighteners; permanent waves; rinses (noncoloring); shampoos (noncoloring); tonics, dressings, and other hair grooming aids; and wave sets, can have a 1,3 propanediol ester concentration ranging between about 0.001% to about 90%, preferably from about 0.01% to about 50%, and more preferably from about 0.05% to about 10%.

Hair coloring preparations such as, for example, hair dyes and colors (requiring caution statement & patch test); hair tints; hair rinses (coloring); hair shampoos (coloring); hair color sprays (aerosol); hair lighteners with color; and hair bleaches, can have a 1,3 propanediol ester concentration ranging between about 0.001% to about 50%, preferably from about 0.1% to about 25%, and more preferably, from about 1% to about 10%.

Makeup preparations (not eye) such as, for example, blushers (all types); face powders; foundations; leg and body paints; lipstick; makeup bases; rouges; and makeup fixatives, can have a 1,3 propanediol ester concentration ranging between about 0.001% to about 99%, preferably from about 0.01% to about 25%, and more preferably from about 0.05% to about 10%.

Manicuring preparations such as, for example, basecoats and undercoats; cuticle softeners; nail creams and lotions; nail extenders; nail polish and enamel; and Nail polish and enamel removers, can have a 1,3 propanediol ester concentration ranging between about 0.001% to about 50%, preferably from about 0.1% to about 10%, and more preferably from about 1% to about 5%.

Oral hygiene products such as, for example, dentifrices (aerosol, liquid, pastes, and powders); and mouthwashes and breath fresheners (liquids and sprays), can have a 1,3 propanediol ester concentration ranging between about 0.001% to about 80%, and more preferably from about 1% to about 5%.

Personal cleanliness products, such as, for example, bath soaps and detergents; deodorants (underarm); antiperspirants; douches; and feminine hygiene deodorants, can have a 1,3 propanediol ester concentration ranging between about 0.001% to about 99%, preferably from about 0.01% to about 50%, and more preferably from about 0.05% to about 10%.

Shaving preparations such as, for example, shaving lotions, aftershave lotions; beard softeners; men's talcum; preshave lotions (all types); shaving cream (aerosol, brushless, and lather); and shaving soap (cakes, sticks, etc.), shaving lotion, can have a 1,3 propanediol ester concentration ranging between about 0.001% to about 50%, preferably from about 0.01% to about 10%, and more preferably from about 0.1% to about 5%.

Skin care preparations (creams, lotions, powder, and sprays), such as, for example, cleansing (cold creams, cleansing lotions, liquids, and pads); depilatories; face and neck (excluding shaving preparations); body and hand (excluding shaving preparations); foot powders and sprays; hormone products; moisturizing; night; paste masks (mud packs); skin lighteners; skin fresheners; and wrinkle-smoothing products (removers), can have a 1,3 propanediol ester concentration ranging between about 0.001% to about 50%, preferably from about 0.01% to about 15%, and more preferably from about 0.05% to about 5%.

Suntan preparations such as, for example, suntan gels, creams, liquids, powders, sticks and sprays; and indoor tanning preparations; can have a 1,3 propanediol ester concentration ranging between about 0.001% to about 75%, and preferably from about 1% to about 25%, and more preferably from about 1% to about 10%.

Preservatives (antiseptic/antifungal/antimicrobial agents), such as, for example, parabens; salicylic acid; sorbic acid; and phenoxy ethanol, can have a 1,3 propanediol ester concentration ranging between about 0.001% to about 100%, and more preferably from about 95% to about 99.99%.

All of the compositions and methods disclosed and claimed herein can be made and executed without undue experimentation in light of the present disclosure. While the compositions and methods of the present disclosure have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents, which are chemically related, may be substituted for the agents described herein while the same or similar results would be achieved. All such similar substitutes and modifications apparent to those skilled in the art are deemed to be within the spirit, scope, and concept of the invention as defined by the appended claims.

EXAMPLES

The present invention is further defined in the following Examples. These Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

The meaning of abbreviations used is as follows: "min" means minute(s), "sec" means second(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "g" means gram(s), "µg" means microgram(s), "mg" means milligram(s), "g" means the gravitation constant, "rpm" means revolutions per minute, "SEM" means standard error of the mean, "vol %" means volume percent and "NMR" means nuclear magnetic resonance.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989.

All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Glycerol used in the production of 1,3-propanediol was obtained from J. T. Baker Glycerin USP grade, Lot J25608 and G19657.

Differential Scanning Calorimetry: DSC thermograms were recorded using Universal V3 1A TA instrument under constant stream of nitrogen with a heating and cooling rate of 10° C./min.

NMR: 1H NMR spectra were recorded on Bruker DRX 500 using XWINNMR version 3.5 software. Data was acquired using a 90 degree pulse (p1) and a 30 second recycle delay (d1). Samples were dissolved in deuterated chloroform and nondeuterated chloroform was used as internal standard.

Isolation and Identifying Bio-PDO:

The conversion of glycerol to bio-PDO was monitored by HPLC. Analyses were performed using standard techniques and materials available to one of skill in the art of chromatography. One suitable method utilized a Waters Maxima 820 HPLC system using UV (210 nm) and RI detection. Samples were injected onto a Shodex SH-1011 column (8 mm×300 mm, purchased from Waters, Milford, Mass.) equipped with a Shodex SH-1011P precolumn (6 mm×50 mm), temperature controlled at 50° C., using 0.01 N H2SO4 as mobile phase at a flow rate of 0.5 mL/min. When quantitative analysis was desired, samples were prepared with a known amount of trimethylacetic acid as external standard. Typically, the retention times of glycerol (RI detection), 1,3-propanediol (RI detection), and trimethylacetic acid (UV and RI detection) were 20.67 min 26.08 min, and 35.03 min, respectively.

Production of bio-PDO was confirmed by GC/MS. Analyses were performed using standard techniques and materials available to one of skill in the art of GC/MS. One suitable method utilized a Hewlett Packard 5890 Series II gas chromatograph coupled to a Hewlett Packard 5971 Series mass selective detector (EI) and a HP-INNOWax column (30 m length, 0.25 mm i.d., 0.25 micron film thickness). The retention time and mass spectrum of 1,3-propanediol generated from glycerol were compared to that of authentic 1,3-propanediol (m/e: 57, 58).

Production of Bio-based Monoesters and Diesters from Bio-produced 1,3-propanediol Monoesters and diester of bio-produced 1,3-propanediol may be produced by combining bio-PDO with organic acid. The combination is to be preformed in dry conditions under heat and prolong agitation with a selected catalyst. The ratio of monoester to diester produced will vary according to the molar ratio of acid to bio-PDO and the selection of catalyst.

The production of esters was confirmed using $^1$H nuclear magnetic resonance. Analyses were performed using standard techniques and materials available to one of skill in the art of $^1$H NMR.

Proton Nuclear Magnetic Resonance ($^1$H NMR) Spectroscopy is a powerful method used in the determination of the structure of unknown organic compounds. It provides information concerning: the number of different types of hydrogens present in the molecule, the electronic environment of the different types of hydrogens and the number of hydrogen "neighbor" a hydrogen has.

The hydrogens bound to carbons attached to electron withdrawing groups tend to resonate at higher frequencies from TMS, tetramethylsilane, a common NMR standard. The position of where a particular hydrogen atom resonates relative to TMS is called its chemical shift ($\delta$). Typical chemicals shifts of fatty ester are as follows.

$\delta$=0.88 for terminal $CH_3$ $\delta$=1.26, 1.61 and 1.97 for methylene groups of ($—CH_2—CH_2—CH_2$), ($CH_2—CH_2—C=O$) and ($O—CH_2—CH_2—CH_2—O$) respectively, $\delta$=2.28 for methylene group adjacent to ester ($CH_2—C=O$)

$\delta$=4.15 for ester ($C(=O)—O—CH_2—$).

Proton NMR can distinguish the protons corresponding to the end groups ($CH_2—OH$) ($\delta$=3.7) from that of the middle ester groups ($CH_2—O—C(=O)—$) ($\delta$=4.15 and 4.24 for diester and monoester, respectively) and thus it is possible to identify ester and can monitor the reaction by comparing the integral areas of these two peaks.

$$\% \text{ Esterification} = \frac{\text{Combined areas of peaks at 41.5 and 4.24} \times 100}{\text{Combined areas of peaks at 3.70, 41.5 and 4.24}}$$

Example 1

Conversion of D-glucose to 1,3-propanediol Under Fermentation Conditions

*E. coli* strain ECL707, containing the *K. pneumoniae* dha regulon cosmids pKP1 or pKP2, the *K. pneumoniae* pdu operon pKP4, or the Supercos vector alone, is grown in a 5 L Applikon fermenter for the production of 1,3-propanediol from glucose.

The medium used contains 50-100 mM potassium phosphate buffer, pH 7.5, 40 mM (NH4)2SO4, 0.1% (w/v) yeast extract, 10 µM CoCl2, 6.5 µM CuCl2, 100 µM FeCl3, 18 µM FeSO4, 5 µM H3BO3, 50 µM MnCl2, 0.1 µM Na2MoO4, 25 µM ZnCl2, 0.82 mM MgSO4, 0.9 mM CaCl2, and 10-20 g/L glucose. Additional glucose is fed, with residual glucose maintained in excess. Temperature is controlled at 37° C. and pH controlled at 7.5 with 5N KOH or NaOH. Appropriate antibiotics are included for plasmid maintenance. For anaerobic fermentations, 0.1 vvm nitrogen is sparged through the reactor; when the dO setpoint was 5%, 1 vvm air is sparged through the reactor and the medium is supplemented with vitamin B12.

Titers of 1,3-propanediol (g/L) range from 8.1 to 10.9. Yields of bio-PDO (g/g) range from 4% to 17%.

Example 2

Purification of Biosourced 1,3-Propanediol 1,3-propanediol, produced as recited in Example 1, was purified, by a multistep process including broth clarification, rotary evaporation, anion exchange and multiple distillation of the supernatant.

At the end of the fermentation, the broth was clarified using a combination of centrifugation and membrane filtration for cell separation, followed by ultrafiltration through a 1000 MW membrane. The clarified broth processed in a large rotary evaporator. Approximately 46 pounds of feed material (21,000 grams) were processed to a concentrated syrup. A 60 ml portion of syrup was placed in the still pot of a 1" diameter distillation column. Distillation was conducted at a vacuum of 25 inches of mercury. A reflux ratio of approximately 1 was used throughout the distillation. Several distillate cuts were taken, the central of which received further processing. The material was diluted with an equal volume of water, the material was loaded onto an anion exchange column (mixed bed, 80 grams of NM-60 resin), which had been water-washed. Water was pumped at a rate of 2 ml/min, with fractions being collected every 9 minutes. Odd number fractions were analyzed, and fractions 3 through 9 contained 3G. The fractions containing 3G were collected and subjected to microdistillation to recover several grams of pure 1,3-propanediol monomer (which was polymerized to mono and diesters according the methods described in Example 2-8).

Example 3

Production of Propanediol Distearate Using p-toluenesulfonic Acid as Catalyst

To prepare propanediol distearate from biosource 1,3-propanediol and stearic acid, bio-source 1,3-propanediol was purified using methods as in examples 1 and 2. 2.58 g (0.033 moles) of biologically-derived 1,3-propanediol, 19.45 g (0.065 moles) of stearic acid (Aldrich, 95%), and 0.2125 g (0.001 moles) of p-toluenesulfonic acid (Aldrich 98.5%) were charged into glass reactor fitted with mechanical stirrer and the reactor was flushed with dry nitrogen gas to remove air and moisture for 15 min. Then reaction temperature was raised to 100° C. while thoroughly stirring the reaction mixture under nitrogen flow and continued for 210 min.

After completion of the reaction, reaction mixture was cooled to about 35° C. and the product was transferred into a beaker. The product was purified by adding 100 mL of water and thoroughly stirring at 45-60° C., to form an emulsion for 15 min. The mixture was cooled and the solid propanediol distearate was separated by filtration.

The product was characterized by $^1$H NMR (Nuclear Magnetic Resonance) spectra ($CDCl_3$ (deuterated chloroform)): $\delta$=0.88 (t, $CH_3$—$CH_2$, 6H), 1.26 (t, $CH_2$—$CH_2$—$CH_2$, 28H), 1.61 (t, $CH_2$—$CH_2$—C=O, 4H), 1.97 (t, —O—$CH_2$—$CH_2$—O, 2H), 2.28 (t, $CH_2$—C=O, 4H), 4.15 (t, C(=O)—O—$CH_2$— 4H) and DSC (Tm=66.4° C. and Tc=54.7° C.). FIG. 1 depicts a graph of these data.

Example 4

Production of Propanediol Distearate Using p-toluenesulfonic Acid as Catalyst

Bio-source 1,3-propanediol was prepared as described herein, specifically as described in Examples 1 and 2. 5.2 g (0.068 moles) of biologically-derived 1,3-propanediol, 38.9 g (0.13 moles) of stearic acid (Aldrich, 95%), and 0.425 g (0.002 moles) of p-toluenesulfonic acid (Aldrich, 98.5%) were charged into glass reactor fitted with mechanical stirrer and the reactor was flushed with dry nitrogen gas to remove air and moisture for 15 min. Then reaction temperature was raised to 130° C. while thoroughly stirring the reaction mixture under nitrogen flow and continued for 195 min at 130° C.

The product was purified as described in Example 3. The product was further purified by dissolving in chloroform and recrystallizing by adding acetone at 15° C. The recrystallized product was filtered and dried.

Figure 3:
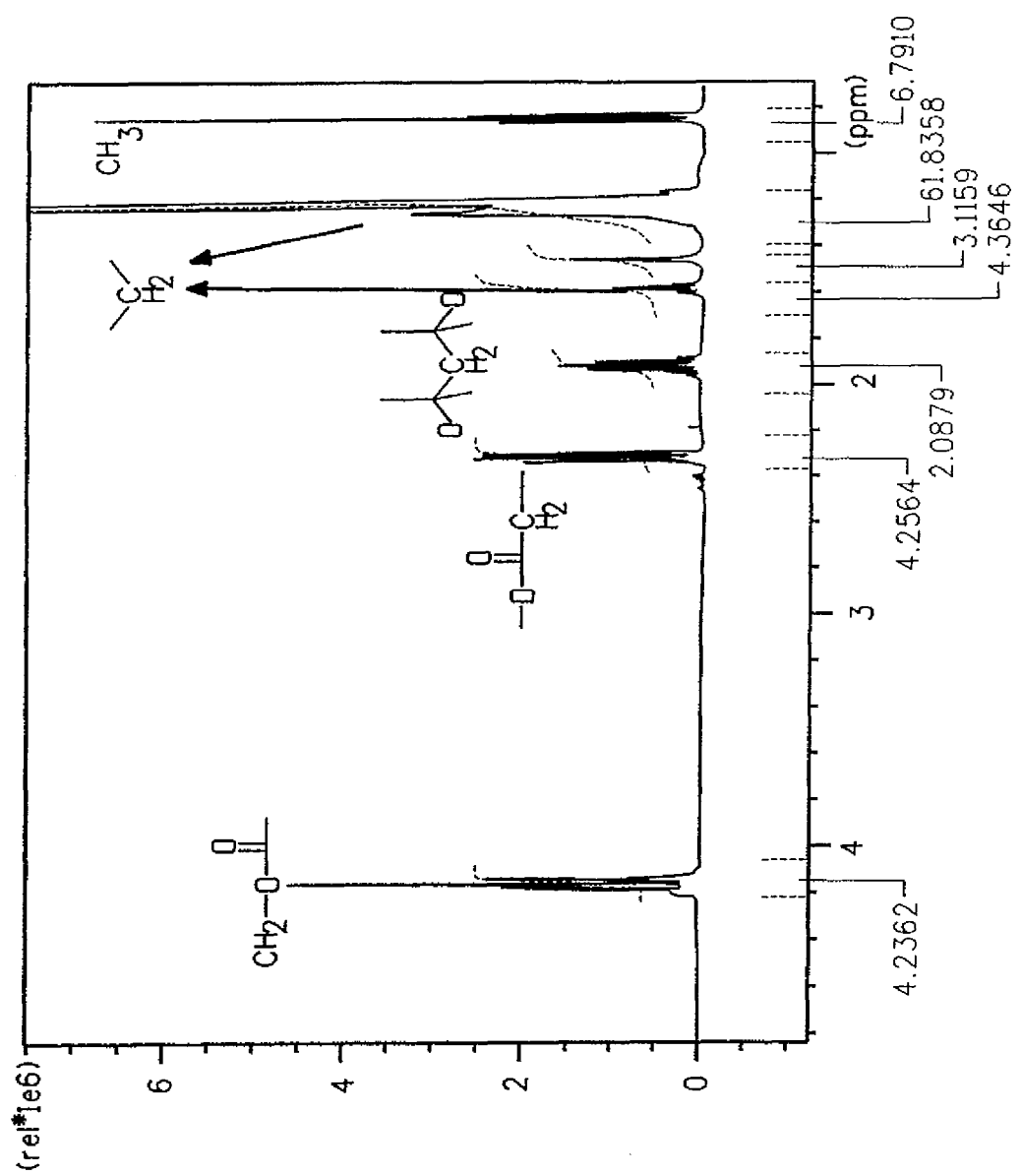
FIG. 3 is diagram of nuclear magnetic resonance spectra of the products obtained in example 4. The figure plots the following values: $\delta$=0.88 (t, $CH_3$—$CH_2$, 6H), 1.26 (t, $CH_2$—$CH_2$—$CH_2$, 28H), 1.61 (t, $\underline{C}H_2$—$CH_2$—C=O, 4H), 1.97 (t, —O—$CH_2$—$CH_2$—$\underline{CH_2}$—O, 2H), 2.28 (t, C$\underline{H_2}$—C=O, 4H), 4.15 (t, $\underline{C}$(=O)—O—$CH_2$— 4H).

The product was characterized by $^1$H NMR spectra ($CDCl_3$): $\delta$=0.88 (t, $CH_3$—$CH_2$, 6H), 1.26 (t, $CH_2$—$CH_2$—$CH_2$, 28H), 1.61 (t, $CH_2$—$CH_2$—C=O, 4H), 1.97 (t, —O—$CH_2$—$CH_2$—$CH_2$—O, 2H), 2.28 (t, $CH_2$—C=O, 4H), 4.15 (t, C(=O)—O—$CH_2$— 4H). FIG. 3 depicts a graph of these data.

Example 5

Production of Propanediol Distearate Using p-toluenesulfonic Acid as Catalyst 39.61 g (0.133 moles) of stearic acid (Aldrich, 95%), 5.05 g (0.066 moles) of biologically derived 1,3-propanediol and 0.46 g (0.0024 moles) of p-toluenesulfonic acid were charged into glass reactor fitted with mechanical stirrer and the reactor was flushed with dry nitrogen gas to remove air and moisture for 15 min. Then reaction temperature was raised to 100° C. while thoroughly stirring the reaction mixture under nitrogen flow. When the reaction temperature reached 100° C., nitrogen flow was shut off and low vacuum was applied to remove by byproduct. The reaction was continued for 2 h. The vacuum was stopped and product was cooled under nitrogen flow.

The product was purified as described in Example 3 and recrystallized as described in Example 4.

Figure 4:
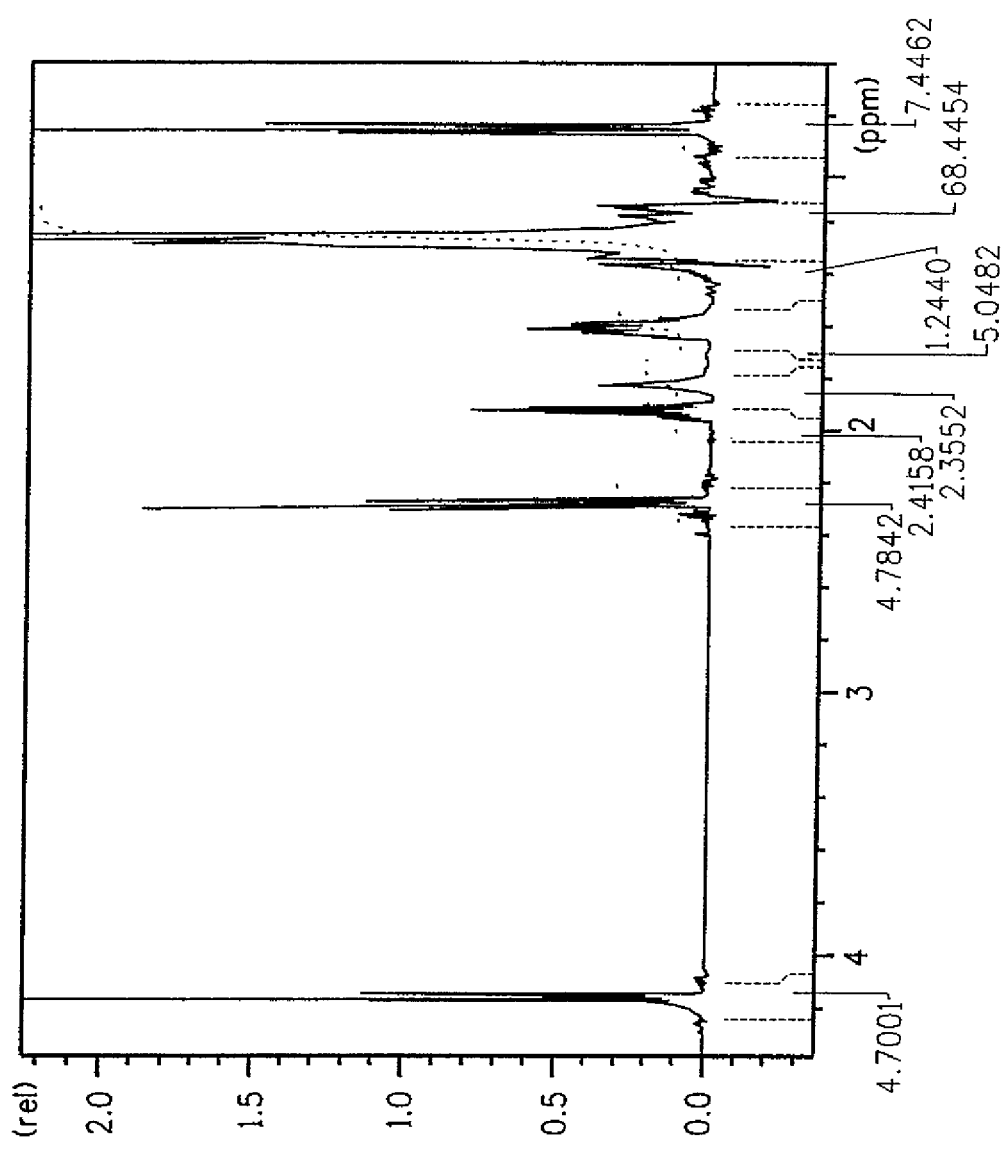
FIG. 4 is diagram of nuclear magnetic resonance spectra of the recrystallized products obtained in example 5. The figure plots the following values $\delta$=0.88 (t, $CH_3$—$CH_2$), 1.27 (t, $CH_2$—$CH_2$—$CH_2$), 1.60 (t, $CH_2$—$CH_2$—C=O), 1.87 and 1.96 (t, —O—$CH_2$—$CH_2$—$\underline{CH_2}$—O,), 2.31 (t, C$\underline{H_2}$—C=O,), 3.70 (t, HO—$\underline{C}H_2$—$CH_2$—), 4.15 and 4.24 (t, $\underline{C}$(=O)—O—$CH_2$—).

The product was characterized by $^1$H NMR spectra ($CDCl_3$): $\delta$=0.88 (t, $CH_3$—$CH_2$, 6H), 1.26 (t, $CH_2$—$CH_2$—$CH_2$, 28H), 1.61 (t, $CH_2$—$CH_2$—C=O, 4H), 1.97 (t, —O—$CH_2$—$CH_2$—$CH_2$—O, 2H), 2.28 (t, $CH_2$—C=O, 4H), 4.15 (t, C(=O)—O—$CH_2$— 4H). FIG. 4 depicts a graph of these data.

Example 6

Production of Propanediol Monostearate and Propanediol Distearate Using Tin Chloride as Catalyst 72.06 g (0.243 moles) of stearic acid (Aldrich, 95%), 9.60 g (0.126 moles) of 1,3-propanediol and 0.25 g of $SnCl_2$ (Aldrich 98%) were charged into glass reactor fitted with mechanical stirrer and the reactor was flushed with dry nitrogen gas to remove air and moisture for 15 min. Then reaction temperature was raised to 120° C. while thoroughly stirring the reaction mixture under nitrogen flow and continued for 240 min.

After completion of the reaction, reaction mixture was cooled and analyzed by NMR. The product contained 39 mole % of propanediol monostearate, 19 mole % of propanediol distearate and 42 mole % 1,3-propanediol.

Figure 5:
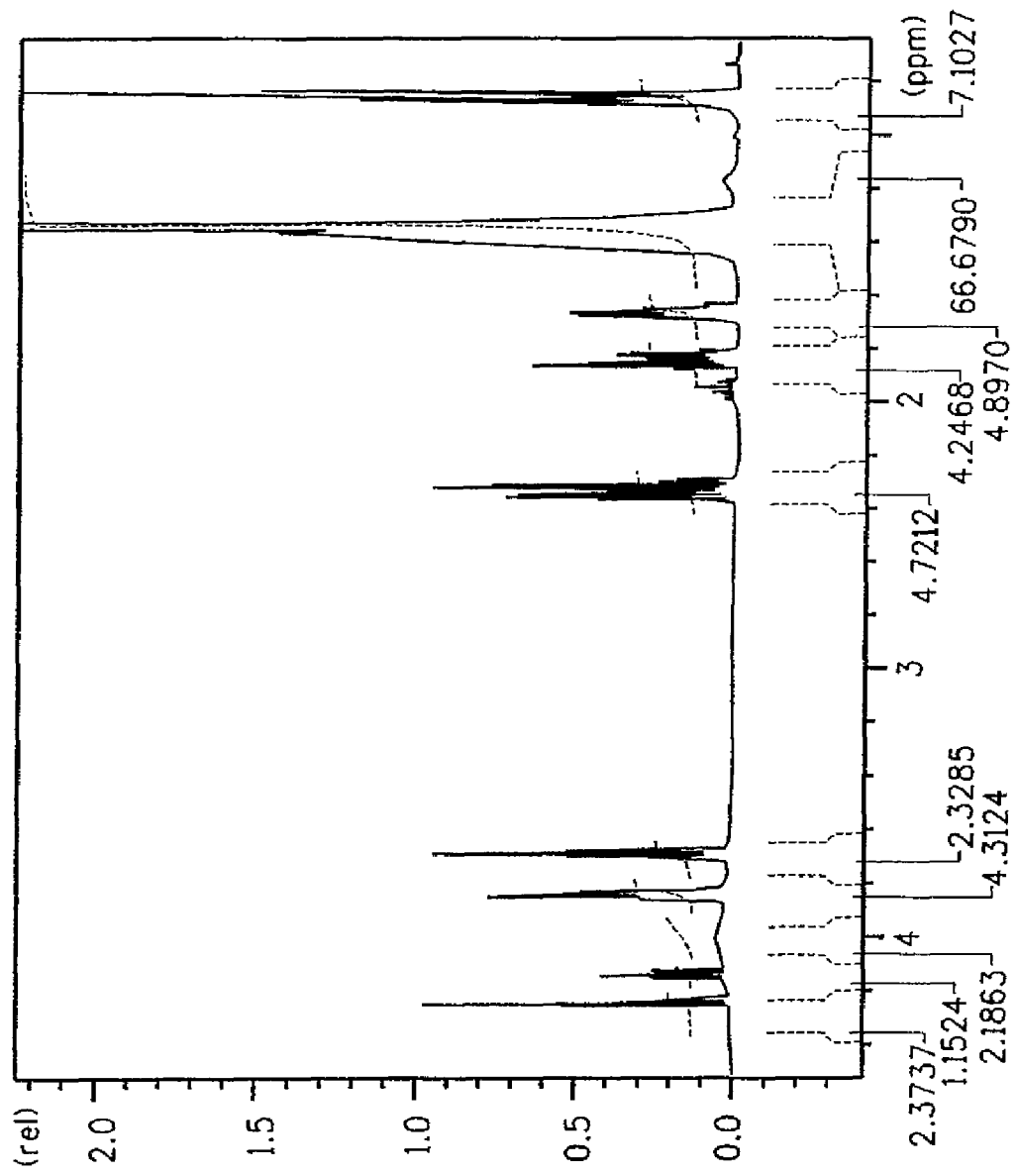
FIG. 5 is diagram of nuclear magnetic resonance spectra of the products obtained in example 6. The figure plots the following values: $\delta$=0.88 (t, $CH_3$—$CH_2$), 1.27 (t, $CH_2$—C$\underline{H_2}$—$CH_2$), 1.63 (t, $CH_2$—$CH_2$—C=O), 1.82, 1.87 and 1.96 (t, —O—$CH_2$—$CH_2$—$\underline{CH_2}$—O,), 2.31 (t, $CH_2$—C=O,), 3.69 and 3.86 (t, HO—$\underline{C}H_2$—$CH_2$—), 4.15 and 4.21 (t, C(=O)—O—$CH_2$—).

$^1$H NMR spectra ($CDCl_3$) $\delta$=0.88 (t, $CH_3$—$CH_2$), 1.27 (t, $CH_2$—$CH_2$—$CH_2$), 1.63 (t, $CH_1$—$CH_2$—C=O), 1.82, 1.87 and 1.96 (t, —O—$CH_2$—$CH_2$—$CH_2$—O,), 2.31 (t, $CH_2$—C=O,), 3.69 and 3.86 (t, HO—$CH_2$—$CH_2$—), 4.15 and 4.21 (t, C(=O)—O—$CH_2$—). FIG. 5 depicts a graph of these data.

Example 7

Production of Propanediol Monostearate and Propanediol Distearate Using Titanium Tetraisopropoxide as Catalyst 35.51 g (0.119 moles) of stearic acid (Aldrich, 95%), 9.55 g (0.125 moles) of 1,3-propanediol and 0.01 g of $Ti(OC_3H_7)_4$ (Aldrich, 99.99%) were charged into glass reactor fitted with mechanical stirrer and the reactor was flushed with dry nitrogen gas to remove air and moisture for 15 min. Then reaction temperature was raised to 170° C. while thoroughly stirring the reaction mixture under nitrogen flow and continued for 240 min. Then the reaction was continued under vacuum for another 30 min. The vacuum was stopped and product was cooled under nitrogen flow and analyzed by NMR.

The product has 36 mole % propanediol monostearate and 64 mole % propanediol distearate.

Figure 6:
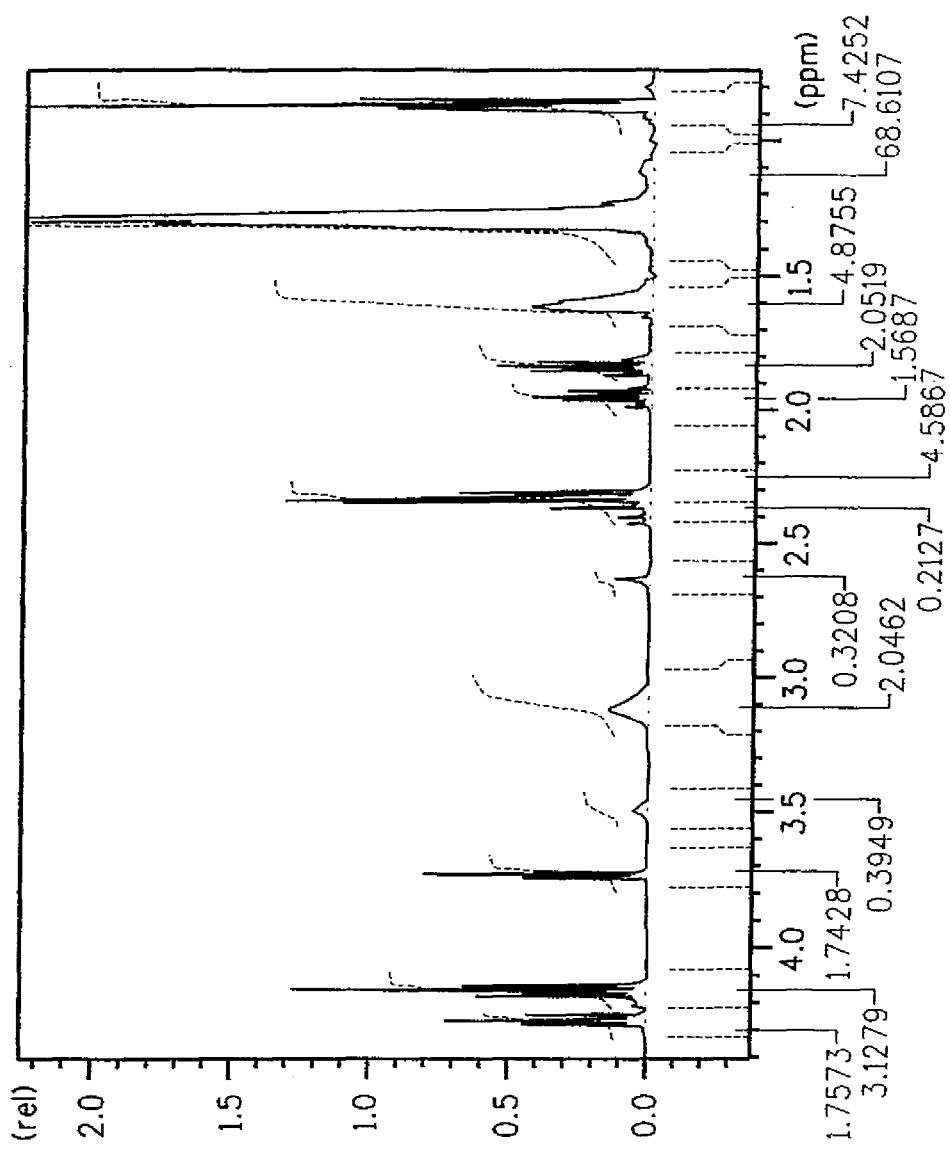
FIG. 6 is diagram of nuclear magnetic resonance spectra of the products obtained in example 7. The figure plots the following values: $\delta$=0.88 (t, $CH_3$—$CH_2$), 1.27 (t, $CH_2$—C$\underline{H_2}$—$CH_2$), 1.60 (t, $CH_2$—$CH_2$—C=O), 1.87 and 1.96 (t, —O—$CH_2$—$CH_2$—$\underline{CH_2}$—O,), 2.31 (t, $CH_2$—C=O,), 3.70 (t, HO—$\underline{C}H_2$—$CH_2$—), 4.15 and 4.24 (t, C(=O)—O—$CH_2$—).

¹H NMR spectra (CDCl3) δ=0.88 (t, CH₃—CH₂), 1.27 (t, CH₂—CH₂—CH₂), 1.60 (t, CH₂—CH₂—C=O), 1.87 and 1.96 (t, —O—CH₂—CH₂—CH₂—O,), 2.31 (t, CH₂C=O,), 3.70 (t, HO—CH₂—CH₂—), 4.15 and 4.24 (t, C(=O)—O—CH₂—). FIG. 6 depicts a graph of these data.

Example 8

Production of Propanediol Monostearate and Propanediol Distearate Using Potassium Acetate as Catalyst 39.72 g (0.133 moles) of stearic acid (Aldrich, 95%), 10.12 g (0.133 moles) of biologically derived 1,3-propanediol and 2.47 g (0.025 moles) of potassium acetate (Aldrich, 99%) were charged into glass reactor fitted with mechanical stirrer and the reactor was flushed with dry nitrogen gas to remove air and moisture for 15 min.

Then reaction temperature was raised to 130° C. while thoroughly stirring the reaction mixture under nitrogen flow. The reaction was continued for 4 h under nitrogen flow. Then the nitrogen flow was shut off and vacuum was applied for 10 min before stopping the reaction. The obtained product was analyzed without further purification.

NMR analysis confirmed the product contained 64.7 mole % of propanediol monostearate, 9.7% mole % of Propanediol distearate and 25.6 mole % 1, 3 Propanediol.

Figure 7:
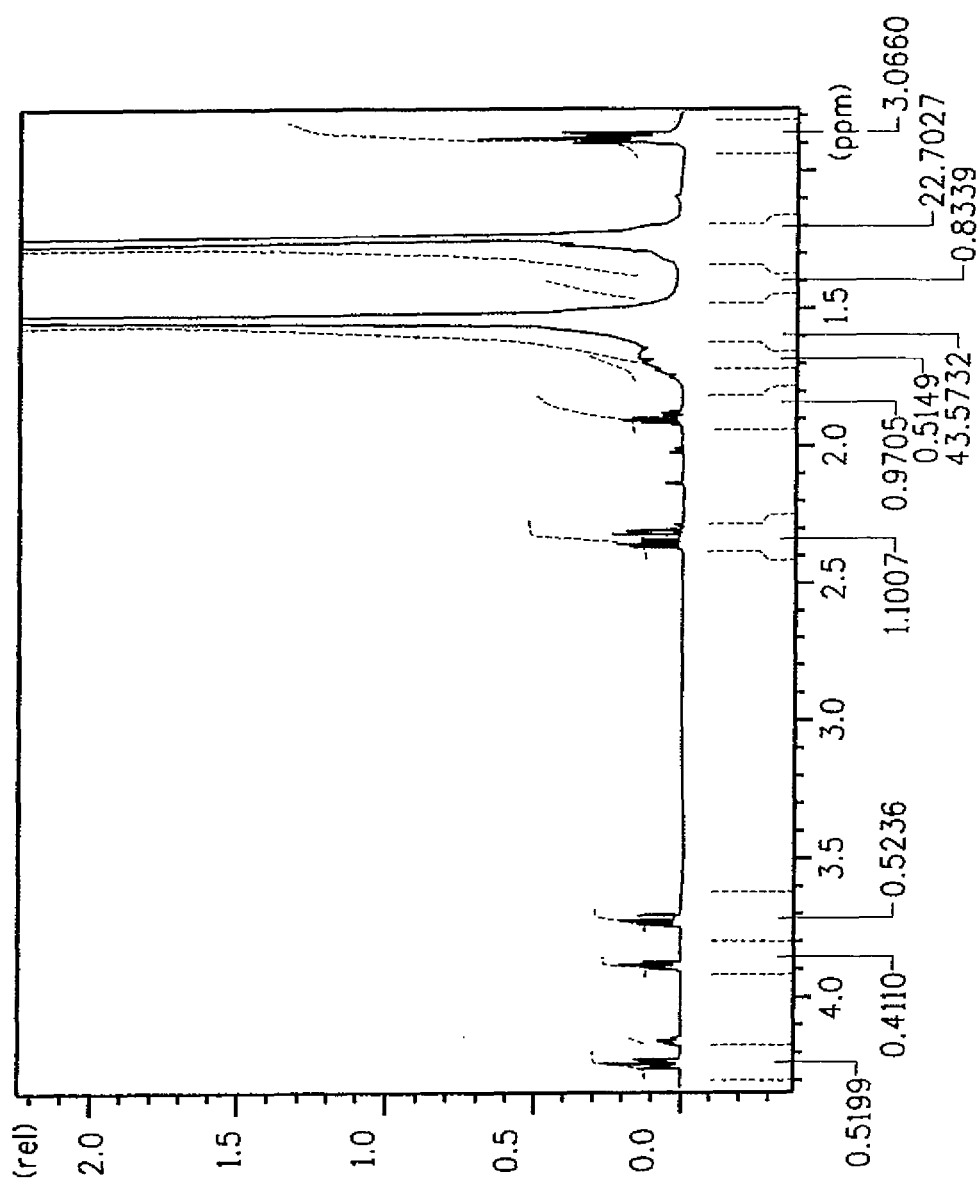
FIG. 7 is diagram of nuclear magnetic resonance spectra of the products obtained in example 8. The figure plots the following values: $\delta$=0.88 (t, $CH_3$—$CH_2$), 1.27 (t, $CH_2$—C$\underline{H_2}$—$CH_2$), 1.63 (t, $CH_2$—$CH_2$—C=O) 1.82, 1.87 and 1.96 (t, —O—$CH_2$—$CH_2$—$\underline{CH_2}$—O,), 2.31 (t, $CH_2$—C=O,), 3.70 and 3.86 (t, HO—$\underline{C}H_2$—$CH_2$—), 4.15 and 4.24 (t, C(=O)—O—$CH_2$—).

¹H NMR spectra (CDCl₃) δ☐=0.88 (t, CH₃—CH₂), 1.27 (t, CH₂—CH₂—CH₂), 1.63 (t, CH₂—CH₂—C=O), 1.82, 1.87 and 1.96 (t, —O—CH₂—CH₂—CH₂—O,), 2.31 (t, CH₂—C=O,), 3.70 and 3.86 (t, HO—CH₂—CH₂—), 4.15 and 4.24 (t, C(=O)—O—CH₂—). FIG. 7 depicts a graph of these data.

Example 9

Production of Propanediol Dilaurate Using p-toluenesulfonic Acid as Catalyst 50.2 g (0.246 moles) of lauric acid (Aldrich, 98%), 9.35 g (0.123 moles) of biologically derived 1,3-propanediol and 0.6 g (0.0031 moles) of p-toluenesulfonic acid (Aldrich 98.5%) were charged into glass reactor fitted with mechanical stirrer and the reactor was flushed with dry nitrogen gas to remove air and moisture for 15 min.

Then reaction temperature was raised to 130° C. while thoroughly stirring the reaction mixture under nitrogen flow. The reaction was continued for 4 h under nitrogen flow. After completion of the reaction, the product was cooled and 90 mL of 0.5 wt % sodium hydroxide solution was added and agitated at 40 to 50° C. for 10 min. Then the product was filtered and thoroughly washed with deionized water and dried.

NMR analysis confirmed the product contained 99.2 mole % of propanediol dilaurate ¹H NMR spectra (CDCl₃) δ☐=0.88 (t, CH₃—CH₂), 1.27 (t, CH₂—CH₂—CH₂), 1.63 (t, CH₂—CH₂—C=O), 1.96 (t, —O—CH₂—CH₂—CH₂—O,), 2.28 (t, CH₂—C=O,), 4.15 (t, C(=O)—O—CH₂)

Example 10

Production of Propanediol Dioleate Using p-toluenesulfonic Acid as Catalyst 51.7 g (0.164 moles) of oleic acid (Aldrich, 90%), 6.26 g (0.082 moles) of biologically derived 1,3-propanediol and 0.6 g (0.0031 moles) of p-toluenesulfonic acid (Aldrich 98.5%) were charged into glass reactor fitted with mechanical stirrer and the reactor was flushed with dry nitrogen gas to remove air and moisture for 15 min.

Then reaction temperature was raised to 130° C. while thoroughly stirring the reaction mixture under nitrogen flow. The reaction was continued for 4 h under nitrogen flow. After completion of the reaction, the product was cooled and 90 mL of 0.5 wt % sodium hydroxide solution was added and agitated at 40 to 50° C. for 10 min.

The mixture was transferred into a separating funnel and 500 mL of deionized water added and mixture was allowed to form two separate layers. Aqueous layer was removed.

Another 500 mL deionized water was added, the solution was mixed and aqueous layer was after two clear layer were formed. The process was repeated for one more time.

NMR analysis confirmed the product contained 99.2 mole % of propanediol dilaurate ¹H NMR spectra (CDCl₃) δ=0.88 (t, CH₃—CH₂), 1.27 and 1.30 (CH₂—CH₂—CH₂), 1.63 (t, CH₂—CH₂—C=O), 1.96 (t, —O—CH₂—CH₂—CH₂—O,), 2.28 (t, CH₂—C=O,), 4.15 (t, C(=O)—O—CH₂—), 5.35 (m CH2-CH=CH—CH2)

Example 11

Liquid Powder Detergent

Using the present invention liquid powder can be prepared using bio-based propanediol caprylate. Obtain the ingredients in the proportionate amounts listing in Table 1. Starting with the ingredients in Table 1, phase A, add inulin lauryl carbamate to water and disperse CARBOPOL ULTREZ 10 (B. F. Goodrich Company, New York, N.Y.). Blend the mixture of phase A ingredients for about 10 minutes, until the carbomer is completely dispersed and hydrated. Under light agitation raise the temperature of the mixture to about 70° C.

In a separate clean container, combine the components listed in Table 1, phase B in the amount stipulated by the table, including bio-based propanediol caprylate, and heat to about 75° C. After the components have been fully combined and are at the target temperature, slowly add phase B mixture to the phase A mixture. Apply rapid agitation and hold temperature between about 70° C. and about 75° C. for 30 minutes. After 30 minutes allow the combined mixtures to cool to 55° C. and with continuous agitation slowly add corn starch of phase C in the amount stipulated by Table 1. When the corn starch has been thoroughly mixed into the combined ingredients of phases A and B, add fragrance and preservative of phase C. Adjust the fragrance and preservative as desired. Measure the pH and then if necessary adjust the pH to between about 5.5 to about 6.0 with triethanolamine. When the pH has been adjusted, cool to room temperature.

TABLE 1

| Ingredients: | % WT. |
| --- | --- |
| Phase A | |
| Water | 55.7 |
| Inulin lauryl carbamate | 0.5 |
| Carbopol Ultrez 10 (Carbomer) | 0.3 |
| Phase B | |
| Neopentyl glycol diheptanoate and isodecane | 5.0 |
| Stearamidopropyl morpholine lactate (25%) | 2.0 |
| Stearyl benzoate | 3.0 |

TABLE 1-continued

| Ingredients: | % WT. |
|---|---|
| Sorbitan oleate | 0.5 |
| Bio-based propanediol caprylate | 0.5 |
| Phase C | |
| Topical Starch (Corn Products corn starch 037570) | 30.0 |
| Fragrance | q.s. |
| Phenoxyethanol and DMDM hydantoin | q.s. |
| Paragon III (Methylparaben and propylparaben) | q.s. |
| Triethanolamine (99%) | q.s. to pH 5.5-6.0 |

Example 12

Pearlized Milk Bath

The present invention can be used to prepare a pearlized milk bath using biobased propanediol distearate. Following the percentages in Table 2, combine UCARE polymer LR-400 with a sufficient amount water to hydrate. Then following the percentage listed in Table 2, blend in PLANTOPON 611 L (Fitz Chem Corporation, Itasca, Ill.) and LAMESOFT PO 65 (Fitz Chem Corporation, Itasca, Ill.) until the mixture reaches uniform consistency.

At this point add polymer solution in the amount listed in Table 2 to the mixture and agitate until uniform consistency is restored. Next following the percentage listed in Table X, add glycerin, STANDAMOX CAW (Fitz Chem Corporation, Itasca, Ill.), NUTRILAN MILK (Fitz Chem Corporation, Itasca, Ill.), bio-based propanediol distearate and mix well until the mixture is again of uniform consistency. Measure the pH and if necessary adjust with citric acid to reach a final pH of between about 6 to about 7. Finally add preservative, dye, fragrance and enough water to reach the desired volume. The final viscosity of the mixture should be between about 5,000 cPs to about 10,000 cPs.

TABLE 2

| Ingredients: | % WT. |
|---|---|
| Plantopon 611 L (Sodium laureth sulfate and lauryl glucoside and cocamidopropyl betaine) | 22.00 |
| Lamesoft PO 65 (Coco glucoside and glyceryl oleate) | 3.00 |
| Standamox CAW (Cocamidopropylamine oxide) | 3.00 |
| Bio-based propanediol distearate | 2.00 |
| Nutrilan Milk (Hydrolyzed milk protein) | 1.50 |
| Emery 917 (Glycerin) | 0.50 |
| Ucare polymer LR-400 (Amerchol) (polyquaterium-10) | 0.10 |
| Water, preservative, fragrance, dye | q.s. |

Example 13

Gentle Baby Shampoo

The present invention can be use in the preparation of a gentle baby shampoo using bio-based propanediol oleate. Obtain the ingredients in the proportionate amounts listed in Table 3. Heat an amount water of slight less than required volume according to Table 3, to about 40° C. Add ingredients in the amount and order listed in Table 3. Mix the ingredients together with gentle agitation, do not exceed 100 rpm. When the mixture has reached uniform consistency, add water to bring the mixture to the desired final volume. The let the mixture cool to room temperature. The resulting shampoo is prepared correctly should appear clear and colorless.

TABLE 3

| Ingredients: | % Wt. |
|---|---|
| Deionized water | q.s. to 100 |
| Tego Betaine L-7 (cocamidopropyl betaine) | 18.5 |
| Neosorb 70/20 (sorbitol) | 16.9 |
| Plantaren 1200 UP (lauryl glucoside) | 15.9 |
| Plantaren 818 UP (coco glucoside) | 12.5 |
| Amisoft LS-11 (sodium lauroyl glutamate) | 5.0 |
| Bio-based propanediol oleate | 2.2 |
| D-panthenol USP (D-panthenol) | 1.0 |
| Sensomer CI-50 (Ondeo Nalco) (hydroxypropyltrimonium chloride) | 0.5 |
| Crotein HKP Powder (keratin amino acid) | 0.4 |
| Fragrance | 0.1 |
| Preservative | q.s. |

Example 14

Moisturizing Body Wash

The present application can be used in the preparation of a moisturizing body wash using bio-based propanediol stearate. To prepare such a moisturizing body wash, start by obtaining the list of ingredients in the proportional amounts listing in Table 4. Mix the together the sodium laureth sulfate, JORDAPON CI (BASF Corporation, Mount Olive, N.J.), AVANEL S150 CGN (BASF Corporation, Mount Olive, N.J.), PEG-150 distearate, Cocamidopropyl betaine, Cocamide MEA, and bio-based propanediol stearate in approximately half of the total water required for the desired volume. After these ingredients thoroughly combined, apply heat to raise the temperature of the mixture to about 65° C. Maintain a temperature of about 65° C. until all components have dissolved and a uniform mixture is obtained. While allowing the mixture to cool, add LUVIQUAT PQ 11 (BASF Corporation, Mount Olive, N.J.) and gently agitate.

In a separate container, mix the CREMOPHOR PS20 (BASF Corporation, Mount Olive, N.J.), vitamin E acetate and fragrance together until fully blended. When the temperature of the first mixture has dropped to below 40° C., add the mixed the CREMOPHOR PS20 (BASF Corporation, Mount Olive, N.J.), vitamin E acetate and fragrance to the mixture. Next added the D,L-PANTHENOL 50 W (BASF Corporation, Mount Olive, N.J.) to the mixture and gently agitate until thoroughly blended. Next add the D,L-Panthenol 50 W to the mixture and gently agitate until thoroughly blended. Next add the disodium EDTA to the mixture and gently agitate until thoroughly blended. Next, add to the mixture a preservative, selected to be adequate for the expected conditions and shelf-life. Finally, add water to bring the mixture to the desired volume, and agitate until an even consistency is achieved.

TABLE 4

| Ingredients: | % Wt. |
|---|---|
| Deionized water | 59.1 |
| Sodium laureth sulfate | 10.0 |
| JORDAPON CI (sodium cocoyl isethionate) | 10.0 |
| AVANEL S150 CGN (sodium C12-15 pareth sulphonate) | 3.0 |
| PEG-150 distearate | 0.5 |
| Cocamidopropyl betaine | 8.0 |
| Cocamide MEA | 3.0 |
| Bio-based propanediol stearate | 2.0 |
| LUVIQUAT PQ11 (polyquaternium-11) | 1.0 |

TABLE 4-continued

| Ingredients: | % Wt. |
|---|---|
| CREMOPHOR PS20 (polysorbate-20) | 2.0 |
| D,L-PANTHENOL 50 W (panthenol) | 0.5 |
| Vitamin E acetate | 0.1 |
| Fragrance | 0.2 |
| Disodium EDTA | 0.5 |
| Preservative | 0.5 |

Example 15

Deep Penetrating Hair Reconstructor

The present invention can be used in the preparation of a deep penetrating hair reconstructor using bio-based propanediol dicaprylate. To prepare such a hair reconstructor obtain the ingredients as listed in and in the relative quantities as depicted in Table 5. Then, mix the DEHYQUART L 80 (Cognis GMBH, Dusseldorf, DE) CETIOL CC (Cognis GMBH, Dusseldorf, DE), DC 949 (Dow Corning, Midland Mich.), GLUADIN WLM (Cognis GMBH, Dusseldorf, DE), perfume, and preservative, i.e. all the components of table 5, phase A. Agitate the component of phase A until completely homogeneous.

In a separate container, disperse the LAMESOFT PW 45 (Grunau Illertissen GmbH, Illertissen, DE) in a quantity of water as shown in Table 5, phase B. When LAMESOFT PW 45 has been fully dispersed add it to the phase A mixture.

In a separate container, mix the bio-based propanediol dicaprylate in deionized water in a quantity of water as shown in Table 5, phase C until a homogeneous cream is obtained. Then, add phase A and B to phase C and agitate until a desire consistency is achieved. If necessary adjust pH to between about 6.5 and about 7.5 using either citric acid or sodium hydroxide.

| Ingredients: | % WT. |
|---|---|
| Phase A | |
| DEHYQUART L 80 | 2.00 |
| (Dicocoylethyl hydroxyethylmonium methosulfate and propylene glycol) | |
| CETIOL CC | 1.00 |
| (Dicaprylyl carbonate) | |
| DC 949 (Dow Corning) | 1.00 |
| (Amodimethicone and cetrimonium chloride and trideceth-12) | |
| GLUADIN WLM | 2.00 |
| (Hydrolized wheat protein) | |
| Perfume | q.s. |
| Preservative | q.s. |
| Phase B | |
| LAMESOFT PW 45 | 4.00 |
| (Cetyl palmitate and beheneth-10 and hydrogenated castor oil and glyceryl stearate) | |
| Water | 37.75 |
| Phase C | |
| Bio-based propanediol dicaprylate | 2.25 |
| Water | 50.00 |

Example 16

Bronzing Stick

The present invention can be used to prepare a bronzing stick using both biobased propanediol myristate and bio-based propanediol diprylate. To prepare such a bronzing stick, obtain all the ingredients in the proportions indicated in Table 6. Combine PEG-8, tocopherol, ascorbyl palmitate, ascorbic acid and citric acid, i.e. all the ingredients of Table 6, Phase C and mix together until homogenized. Combine the ingredients of Phase C, with the microcrystalline wax SP-1028 (Strahl & Pitsch, Inc., West Babylon, N.Y.), lauryl laurate (Strahl & Pitsch, Inc., West Babylon, N.Y.), microcrystalline wax SP-89 (Strahl & Pitsch Inc., West Babylon, N.Y.), microcrystalline wax SP-19 (Strahl & Pitsch Inc., West Babylon, N.Y.), caprylic/capric triglycerides (Cognis GMBH, Dusseldorf, DE), bio-based propandiol myristate, bio-based propanediol diprylate, Trioctyldodecyl citrate (Phoenix, Merseyside, UK), and Propylparaben (Spectrum Chemical Manufacturing Corporation, Gardena, Calif.). Mix the combination while heating. Bring the combination to about 85° C. under continuous agitate. Maintain 85° C. until the mixture has reached homogeny.

In a separate container, mix together the Colorona bronze cosmetic pigment (Rona Cosmetics GmBH, Darmstadt DE), Timiron MP-10 cosmetic pigment (Rona Cosmetics GmBH, Darmstadt DE), Colorona copper cosmetic pigment (Rona Cosmetics GmBH, Darmstadt DE), and Biron LF-2000 cosmetic pigment (Rona Cosmetics GmBH, Darmstadt DE), i.e. all the components of Table 6, phase B. When the phase B components have been thoroughly mixed, blend them into the already combined phase A and phase C mixture, while continuing to heat at 85° C. After the phase B mixture has been thoroughly combined with phase A and phase C and homogeny has reached, allow the mixture to cool to between about 70° C. and about 80° C. While the mixture is between about 70° C. and about 80° C., pour the mixture into molds to create sticks. Allow the mixture to fully cool to room temperature before removing the formed sticks from the molds.

TABLE 6

| Ingredients: | % WT. |
|---|---|
| Phase A | |
| Microcrystalline wax SP-1028 (Strahl & Pitsch) | 11.70 |
| Lauryl laurate (Strahl & Pitsch) | 3.00 |
| Microcrystalline wax SP-89 (Strahl & Pitsch) | 2.80 |
| Microcrystalline wax SP-19 (Strahl & Pitsch) | 2.80 |
| Caprylic/capric triglycerides (Cognis) | 14.00 |
| Bio-based propandiol myristate | 15.00 |
| Bio-based propanediol diprylate | 19.40 |
| Trioctyldodecyl citrate (Phoenix) | 3.00 |
| Propylparaben (Spectrum Chemical) | 0.20 |
| Phase B | |
| Colorona bronze cosmetic pigment (Mica and iron oxides) | 13.00 |
| Timiron MP-10 cosmetic pigment (Mica and titanium oxides) | 9.00 |
| Colorona copper cosmetic pigment (Mica and iron oxides) | 3.00 |
| Biron LF-2000 cosmetic pigment (Bismuth oxychloride) | 3.00 |
| Phase C | |
| PEG-8 | 0.02 |
| tocopherol | 0.02 |
| ascorbyl palmitate | 0.02 |
| ascorbic acid | 0.02 |
| citric acid | 0.02 |

Example 17

Lip Gloss

Mix caster oil, bio-based propanediol distearate, cetyl alcohol and heat the mixture to 75° C. until a uniform solution is formed. Add color pigment and heat the mixture while stirring till no lumps are remained. Add TiO$_2$ and heat to 85° C. with stirring until a uniform product is formed. Add fragrance while cooling and transfer into containers.

| Ingredients | Wt % |
|---|---|
| Phase A | |
| Caster oil | 55.0 |
| Bio-based propanediol distearate | 16.0 |
| Cetyl alcohol[1] | 1.6 |
| Pigment (iron oxide)[2] | 1.5 |
| TiO$_2$ | 25.4 |
| Fragrance | QS |

[1]The Chemistry Store.com, Cayce, SC
[2]Somerset Cosmetic Co. LLC, Renton, WA

Example 18

Pearlized Milk Bath

Poly(diallyidimethylammonium chloride), 20 wt % in water was blended with PLANTOPON 611 L, polyglucoside, bio-based 1,3-propanediol oleate and cocamide DMA in the proportional amounts listed in Table until the mixture reaches uniform consistency. Then glycerin, milk protein, bio-based 1,3-propanediol oleate, bio-based 1,3-propanediol distearate were added and mixed well until the mixture is again of uniform consistency. Measure the pH and if necessary adjust with citric acid to reach a final pH of between about 6 to about 7. Finally add preservative, dye, fragrance and enough water to reach the desired volume. The final viscosity of the mixture should be between about 5,000 cPs to about 10,000 cPs.

| Ingredients: | % Wt. |
|---|---|
| Plantopon 611 L[3] | 22.00 |
| Polyglucose (decyl glucoside)[2] | 3.00 |
| Cocamide DMA[1] | 3.00 |
| Bio-based propanediol oleate | 0.50 |
| Bio-based propanediol distearate | 2.00 |
| Milk protein | 1.50 |
| Glycerin | 0.50 |
| Poly(diallyldimethylammonium chloride), (20 wt % in water)[4] | 1.00 |
| Water, preservative, fragrance, dye | q.s. |

[1]The Chemistry Store.com, Cayce, SC
[2]Somerset Cosmetic Co. LLC, Renton, WA
[3]Fitz Chem Corporation, Itasca, IL
[4]Sigma-Aldrich, Milwaukee, WI Example 19

Moisturizing Body Wash

Mix the together the blend 213 (Chemistry Store), Cocamidopropyl betaine, Cocamide DEA, and bio-based propanediol distearate. After these ingredients thoroughly combined, apply heat to raise the temperature of the mixture to about 70° C. Maintain a temperature of about 70° C. until all components have dissolved and a uniform mixture is obtained. While allowing the mixture to cool, add poly(diallyidimethylammonium chloride) solution and gently agitate. When the temperature of the first mixture has dropped to below 40° C., add the polysorbate-60, vitamin E acetate to the mixture. Next added the Panthenol to the mixture and gently agitate until thoroughly blended. Next add the disodium EDTA to the mixture and gently agitate until thoroughly blended. Next, add to the mixture a preservative, fragrance and water to bring the mixture to the desired volume, and agitate until an even consistency is achieved.

| Ingredients: | % Wt. |
|---|---|
| Blend 213[1] | 47.0 |
| Sodium Laureth Sulfate | |
| Cocamidopropyl Betaine | |
| Cocamide DEA | |
| PEG-150 Distearate | |
| Cocamidopropyl Betaine[1] | 4.0 |
| Cocamide DEA[1] | 3.0 |
| bio-based 1,3-propanediol distearate | 2.0 |
| Poly(diallyldimethylammonium chloride), (20 wt % in water)[4] | 5.0 |
| Polysorbate-60[2] | 2.0 |
| Panthenol | 0.5 |
| Vitamin E acetate | 0.1 |
| Disodium EDTA | 0.5 |
| Preservative | 0.5 |
| D.I Water, Fragrance | q.s. |

[1]The Chemistry Store.com, Cayce, SC
[2]Somerset Cosmetic Co. LLC, Renton, WA
[3]Fitz Chem Corporation, Itasca, IL
[4]Sigma-Aldrich, Milwaukee, WI Example 20

Bronzing Stick

Mix the ingredients of Phase A. Heat the mixture to about 70° C. under continuous agitation. Maintain 70° C. until the mixture has reached homogeneous.

In a separate container, mix together the TiO$_2$, and pigment(s) and blend them into the phase A mixture, while continuing to heat at 70° C. After the phase B mixture has been thoroughly combined with phase A and homogeny has reached, allow the mixture to cool to about 50° C., pour the mixture into molds to create sticks. Allow the mixture to fully cool to room temperature before removing the formed sticks from the molds.

| Ingredients | Wt % |
|---|---|
| Phase A | |
| Emulsifying Wax NF[1] | 17.42 |
| bio-based 1,3-propanediol distearate | 18.13 |
| bio-based 1,3-propanediol dilaurate | 14.10 |
| bio-based 1,3-propanediol dicaprylate | 19.54 |
| Cetyl alcohol[1] | 2.27 |
| Germaben II[1] | 0.20 |
| PEG-8 | 0.02 |
| Citric acid | 0.12 |
| Phase B | |
| TiO2 | 25.18 |
| Pigment (Iron oxide)[2] | 3.02 |

[1]The Chemistry Store.com, Cayce, SC
[2]Somerset Cosmetic Co. LLC, Renton, WA

Example 21

Hand Cleanser

Blend ammonium lauryl sulfate, cocamide DEA, sodium lauryl sulfate solution and BioPDO™ at room temperature. Add BioPDO™ stearate and Irgsan. Heat to 60° C. while stirring until solids are dissolved. Cool to 30° C., add EDTA. Stir until a homogeneous solution is formed. Adjust to pH 6 with citric acid. Add fragrance.

| Ingredient | Wt. % |
|---|---|
| Ammonium Lauryl Sulfate (ALS) (28%) | 26.0 |
| Cocamide DEA [2] | 6.0 |
| Sodium Lauryl Sulfate (SLS) (25%) | 18.0 |
| Biologically-derived 1,3-propanediol | 1.0 |
| Water | 44.5 |
| Bio-based 1,3-propanediol stearate | 0.5 |
| Irgasan [6] | 0.2 |
| Tetrasodium EDTA (5 wt %) | 2.0 |
| Citric acid (50 wt %) | QS |
| Fragrance | 0.2 |

[1] DuPont Tate & Lyle Bio Products
[2] The Chemistry Store.com, Cayce, SC
[3] Somerset Cosmetic Co. LLC, Renton, WA
[4] Stephan Co. Northfield, IL
[5] Noveon, Cleveland, OH
[6] Sigma-Aldrich, Milwaukee, WI Example 22

Sunscreen

Combine components of phase A mix and heat to 75° C. In a separate container mix the components of phase B and heat to 75° C. Combine phase B with phase A. Cool it to 45° C. Add components of phase C. Mix it thoroughly. Add components of phase D and E. Mix it until viscosity developed.

| Ingredients | Wt % |
|---|---|
| Phase A | |
| Deionized water | 58.01 |
| Carbopol 934 (Noveon, Cleveland, OH) | 0.40 |
| Disodium EDTA | 0.125 |
| Biologically-derived 1,3-propanediol | 4.00 |
| Phase B | |
| Oxybenzone [3] | 15.50 |
| Phenylethyl benzoate | 10.00 |
| Bio-based 1,3-propanediol stearate | 2.00 |
| Ceteareth [3] | 2.00 |
| Phase C | |
| Deionized water | 5.00 |
| TEA | 0.50 |
| Phase D | |
| Germaben II [2] | 1.65 |
| Biologically-derived 1,3-propanediol [1] | 0.50 |
| Phase E | |
| Idopropynyl butylcarbamate | 0.20 | pH: 7; Viscosity: 12700 @ 30 rpm
[1] DuPont Tate & Lyle Bio Products
[2] The Chemistry Store.com, Cayce, SC
[3] Somerset Cosmetic Co. LLC, Renton, WA
[4] Stephan Co. Northfield, IL
[5] Noveon, Cleveland, OH
[6] Sigma-Aldrich, Milwaukee, WI Example 23

Skin Cream

| Ingredients | wt % |
|---|---|
| Water | 73.3 |
| Stearic Acid | 15.0 |
| Petroleum jelly | 2.0 |
| Biologically-derived 1,3-propanediol | 5.00 |
| Bio-based 1,3-propanediol monoisostearate | 3.0 |
| Polyoxyethylene cetyl ether | 1.0 |
| Perfume | q.s. |

What is claimed:

1. A method of reducing the atmospheric $CO_2$ emission of a personal care composition upon biodegradation, the method comprising:
preparing a personal care composition comprising an ester wherein said ester is a 1,3-propanediol ester, wherein said 1,3-propanediol portion of said ester is biologically-derived, biodegradable, and exhibits no atmospheric $CO_2$ emission upon biodegradation, and
using said personal care composition whereby said personal care composition biodegrades, wherein said reduction of atmospheric $CO_2$ emission is compared to the atmospheric $CO_2$ emission of a personal care composition not comprising an ester wherein said ester is a 1,3-propanediol ester, wherein said 1,3-propanediol portion of said ester is biologically-derived and biodegradable.

2. The method of claim 1, wherein said ester has at least 3% biobased carbon.

3. The method of claim 1, wherein said ester comprises a radiocarbon signature of at least 3.225 pMC when calculated according to the ASTM-D6866 method.

4. The method of claim 1, wherein said ester has the formula R1-C(=O)—O—CH2-CH2-CH2-OH, wherein R1 is a linear or branched carbon chain of a length between 1 and 40 carbons.

5. The method of claim 4, wherein R1 has one or more functional groups selected from the group consisting of alkene, amide, amine, carbonyl, carboxylic acid, halide, hydroxyl groups, ether, alkyl ether, sulfate and ethersulfate.

6. The method of claim 1 wherein said ester has the formula R1-C(=O)—O—CH2-CH2-CH2-O—C(=O)—R2, wherein R1 and R2 are linear or branched carbon chains of a length between 1 and 40 carbons.

7. The method of claim 6, wherein R1 and R2 have one or more functional groups selected from the group consisting of alkene, amide, amine, carbonyl, carboxylic acid, halide, hydroxyl groups, ether, alkyl ether, sulfate and ethersulfate.

8. The method of claim 7 wherein R1 and R2 are the same carbon chain.

9. The method of claim 1 wherein said ester is selected from the group consisting of:
i. propanediol distearate, monostearate and a mixture thereof;
ii. propandiol dilaurate, monolaurate and a mixture thereof;
iii. propanediol dioleate, monooleate and a mixture thereof;
iv. propanediol divalerate, monovalerate and a mixture thereof;

v. propanediol dicaprylate, monocaprylate and a mixture thereof;
vi, propanediol dimyristate, monomyristate and a mixture thereof;
vii. propanediol dipalmitate, monopalmitate and a mixture thereof;
viii. propanediol dibehenate, monobehenate and a mixture thereof;
ix. propanediol adipate;
x. propanediol maleate;
xi. propanediol dibenzoate;
xii. propanediol diacetate; and
xiii. mixtures thereof.

10. The method of claim 1, wherein said personal care composition comprises between about 0.5% and about 80% by weight of the ester.

11. The method of claim 1, wherein said personal care composition further comprises 1,3-propanediol.

12. The method of claim 11, wherein said 1,3-propanediol is biologically-derived.

13. The method of claim 12, wherein said 1,3-propanediol has at least 95% biobased carbon content.

14. A method of reducing the atmospheric $CO_2$ emission of a personal care composition upon degradation, the method comprising:
preparing a personal care composition comprising an ester wherein said ester is a biologically-derived, biodegradable 1,3-propanediol ester, and wherein said biologically-derived, biodegradable 1,3-propanediol exhibits no atmospheric $CO_2$ emission upon biodegradation, and
using said personal care composition whereby said personal care composition biodegrades, wherein said reduction of atmospheric $CO_2$ emission is compared to the atmospheric $CO_2$ emission of a personal care composition not comprising biologically-derived, biodegradable 1,3-propanediol ester.

* * * * *